US011521704B2

(12) United States Patent
Schiffer et al.

(10) Patent No.: US 11,521,704 B2
(45) Date of Patent: Dec. 6, 2022

(54) METHOD FOR PROBING AT LEAST ONE BINDING SITE OF A PROTEIN

(71) Applicant: University of Massachusetts, Boston, MA (US)

(72) Inventors: Celia A. Schiffer, Shrewsbury, MA (US); Florian Leidner, Worcester, MA (US); Troy W. Whitfield, Wellesley, MA (US); Debra A. Ragland, Carrboro, NC (US); Nese Kurt Yilmaz, Shrewsbury, MA (US); Konstantin B. Zeldovich, Belmont, MA (US); Aysegul Ozen, Mystic, CT (US)

( * ) Notice: Subject to any disclaimer, the term of this patent is extended or adjusted under 35 U.S.C. 154(b) by 1035 days.

(21) Appl. No.: 16/045,454

(22) Filed: Jul. 25, 2018

(65) Prior Publication Data

US 2019/0065667 A1    Feb. 28, 2019

Related U.S. Application Data

(60) Provisional application No. 62/536,930, filed on Jul. 25, 2017.

(51) Int. Cl.
*G01N 31/00* (2006.01)
*G16B 5/00* (2019.01)
*G16B 15/30* (2019.01)

(52) U.S. Cl.
CPC ............. *G16B 5/00* (2019.02); *G16B 15/30* (2019.02)

(58) Field of Classification Search
None
See application file for complete search history.

(56) References Cited

U.S. PATENT DOCUMENTS

| | | |
|---|---|---|
| 2010/0049689 A1 | 2/2010 | Jorg et al. |
| 2010/0173381 A1 | 7/2010 | Schiffer et al. |
| 2010/0241411 A1 | 9/2010 | Young et al. |
| 2011/0172981 A1 | 7/2011 | Al-Hashimi et al. |
| 2012/0116742 A1 | 5/2012 | Prakash et al. |
| 2015/0142398 A1 | 5/2015 | Miller |
| 2017/0032078 A1 | 2/2017 | Stelzer et al. |

OTHER PUBLICATIONS

Guan, Jia-Ying, et al. "Small-molecule binding sites on proteins established by paramagnetic NMR spectroscopy." Journal of the American Chemical Society 135.15 (2013): 5859-5868.*
Durrant, Jacob D., and J. Andrew McCammon. "Molecular dynamics simulations and drug discovery." BMC biology 9.1 (2011): 1-9.*
Brooks, Bernard R., et al. "CHARMM: a program for macromolecular energy, minimization, and dynamics calculations." Journal of computational chemistry 4.2 (1983): 187-217.*
Lee, Hwankyu, et al. "Molecular dynamics studies of polyethylene oxide and polyethylene glycol: hydrodynamic radius and shape anisotropy." Biophysical journal 95.4 (2008): 1590-1599.*
Bowers, Kevin J., et al. "Scalable algorithms for molecular dynamics simulations on commodity clusters." SC'06: Proceedings of the 2006 ACM/IEEE Conference on Supercomputing. IEEE, 2006.*
Harte, W. E., et al. "Domain communication in the dynamical structure of human immunodeficiency virus 1 protease." Proceedings of the National Academy of Sciences 87.22 (1990): 8864-8868.*
Oferkin, Igor Vladimirivich, et al. "Evaluation of the docking algorithm based on tensor train global pptimization." Bulletin of the South Ural State University. Series: Mathematical modeling and programming 8.4 (2015): 83-99.*
Ding, Feng, and Nikolay V. Dokholyan. "Simple but predictive protein models." Trends in biotechnology 23.9 (2005): 450-455.*
Deng, Yuqing, and Benoît Roux. "Computations of standard binding free energies with molecular dynamics simulations." The Journal of Physical Chemistry B 113.8 (2009): 2234-2246.*
Joughin, Brian A., David F. Green, and Bruce Tidor. "Action-at-a-distance interactions enhance protein binding affinity." Protein science 14.5 (2005): 1363-1369.*
Dokholyan, Nikolay V., et al. "Discrete molecular dynamics studies of the folding of a protein-like model." Folding and design 3.6 (1998): 577-587.*
Altschul, S. F.et al., "Basic Local Alignment Search Tool," J. Mol. Biol. 1990, 215, 403-410.
Berendsen, H. J. C. et al., "Molecular dynamics with coupling to an external bath," J. Chem. Phys. 1984, 81, 8, 3684-3690.
Bowers, K. J. et al., "Scalable Algorithms for Molecular Dynamics Simulations on Commodity Clusters," Proceedings of the 2006 ACM/IEEE Conference on Supercomputing 2006, 84.
De Meyer, S. et al., "TMC114, a Novel Human Immunodeficiency Virus Type 1 Protease Inhibitor Active against Protease Inhibitor-Resistant Viruses, Including a Broad Range of Clinical Isolates," Antimicrob. Agents and Chemother. 2005, 49, 6, 2314-2321.
Essmann, U. et al., "A smooth particle mesh Ewald method," J. Chem. Phys. 1995, 103, 19, 8577-8593.
Gianni, S. et al., "Demonstration of Long-Range Interactions in a PDZ Domain by NMR, Kinetics, and Protein Engineering," Structure 2006, 14, 1801-1809.
Guo, Z. et al., "Probing the α-Helical Structural Stability of Stapled p53 Peptides: Molecular Dynamics Simulations and Analysis," Chem. Biol. Drug Des. 2010, 75, 348-359.
Hoffman, N. G. et al., "Covariation of amino acid positions in HIV-1 protease," Virology 2003, 314, 536-548.
Humphrey, W. et al., "VMD: Visual Molecular Dynamics," J. Mol. Graphics 1996, 14, 33-38.

(Continued)

*Primary Examiner* — Anna Skibinsky
(74) *Attorney, Agent, or Firm* — Hamilton, Brook, Smith & Reynolds, P.C.

(57) ABSTRACT

At least one binding site of a protein is probed by calculating a set of molecular dynamic trajectories of a protein-ligand complex family. At least one script is applied to the molecular dynamic trajectories to form a set of tensors, and at least one second script is applied to the set of tensors to integrate the set of tensors with experimental binding data corresponding to the protein-ligand complex family to form a primary image of the binding site, thereby probing the binding site of the protein.

25 Claims, 16 Drawing Sheets

Specification includes a Sequence Listing.

(56) References Cited

OTHER PUBLICATIONS

Humphris-Narayanan, E. et al., "Prediction of Mutational Tolerance in HIV-1 Protease and Reverse Transcriptase Using Flexible Backbone Protein Design," PLoS Comput. Biol. 2012, 8, 8, e1002639.
Jabara, C. B. et al., "Accurate sampling and deep sequencing of the HIV-1 protease gene using a Primer ID," Proc. Natl. Acad. Sci. U.S.A. 2011, 108, 50, 20166-20171.
Jorgensen, W. L. et al., "Comparison of simple potential functions for simulating liquid water," J. Chem. Phys. 1983, 79, 2, 926-935.
King, N. M. et al., "Structural and Thermodynamic Basis for the Binding of TMC114, a Next-Generation Human Immunodeficiency Virus Type 1 Protease Inhibitor," J. of Virol. 2004, 78, 21, 12012-12021.
King, N. M. et al., "Combating Susceptibility to Drug Resistance: Lessons from HIV-1 Protease," Chemistry & Biology 2004, 11, 1333-1338.
Kozisek, M. et al., "Thermodynamic and structural analysis of HIV protease resistance to darunavir-analysis of heavily mutated patient-derived HIV-1 proteases," FEBS J. 2014, 281, 1834-1847.
Leidner, F. et al., "Hydration Structure and Dynamics of Inhibitor-Bound HIV-1 Protease" J. Chem. Theory Comput., 2018, 14, 2784-2796.
Logsdon, B. C. et al., "Crystal Structures of a Multidrug-Resistant Human Immunodeficiency Virus Type 1 Protease Reveal an Expanded Active-Site Cavity," J. Virol. 2004, 78, 6, 3123-3132.
Mahalingam, B. et al., "Combining Mutations in HIV-1 Protease to Understand Mechanisms of Resistance," Proteins: Struct., Funct., Genet. 2002, 48, 107-116.
Martyna, G. J. et al., "Constant pressure molecular dynamics algorithms," J. Chem. Phys. 1994, 101, 5, 4177-4189.
Meher, B. R. and Wang, Y., "Interaction of I50V Mutant and I50L/A71V Double Mutant HIV-Protease with Inhibitor TMC114 (Darunavir): Molecular Dynamics Simulation and Binding Free Energy Studies," J. Phys. Chem. B 2012, 116, 6, 1884-1900.
Mittal, S. et al., "Structural and Thermodynamic Basis of Amprenavir/Darunavir and Atazanavir Resistance in HIV-1 Protease with Mutations at Residue 50," J. Virol. 2013, 87, 4176-4184.
Nalam, M. N. et al., "Evaluating the Substrate-Envelope Hypothesis: Structural Analysis of Novel HIV-1 Protease Inhibitors Designed to Be Robust against Drag Resistance," J. Virol. 2010, 84, 10, 5368-5378.
Narayanan, C. et al., "Applications of NMR and computational methodologies to study protein dynamics," Arch. Biochcm. Biophys. 2017, 628, 71-80.
Nijhuis, M. et al., "Increased fitness of drag resistant HIV-1 protease as a result of acquisition of compensatory mutations during suboptimal therapy," AIDS 1999, 13, 2349-2359.
Notification of Transmittal of the International Search Report and Written Opinion for International Application No. PCT/US2018/043712, entitled: "Method for Probing at Least One Binding Site of a Protein," dated Nov. 9, 2018.
Ozen, A. et al., "Improving the Resistance Profile of Hepatitis C NS3/4A Inhibitors: Dynamic Substrate Envelope Guided Design," J. Chem. Theory Comput. 2013, 9, 12, 5693-5705.
Paulsen, J. L. et al., "Interdependence of Inhibitor Recognition in HIV-1 Protease," J. Chem. Theory Comput. 2017, 13, 2300-2309.
Prachanronarong, K.L. et al., "Molecular Basis for Differential Patterns of Drug Resistance in Influenza N1 and N2 Neuraminidase," J. Chem. Theory Comput. 2016, 12, 6098-6108.
Prezista [Package Insert]; Janssen Therapeutics: Titusville, NJ, Revised Jun. 2017.
Ragland, D.A. et al., "Drug Resistance Conferred by Mutations Outside the Active Site Through Alterations in the Dynamic Structural Ensemble of HIV-1 Protease," J. Am. Chem. Soc. 2014, 136, 11956-11963.
Ragland, D.A. et al., "Elucidating the Interdependence of Drug Resistance from Combinations of Mutations," J. Chem. Theory Comput. 2017, 13, 5671-5682.
Rhee, S.-Y. et al., "Human immunodeficiency virus reverse transcriptase and protease sequence database," Nucleic Acids Res. 2003, 31, 1, 298-303.
Shafer, R. W., "Rationale and Uses of a Public HIV Drug-Resistance Database." J. Infect. Dis. 2006, 194, S51-S58.
Sinha, N. and Smith-Gill, S. J., "Protein Structure to Function Via Dynamics," Protein Pept. Lett. 2002, 9, 5, 367-377.
Soumana, D.I., et al., "Molecular and Dynamic Mechanism Underlying Drug Resistance in Genotype 3 Hepatitis C NS34A Protease," J. Am. Chem. Soc. 2016, 138, 11850-11859.
Tamura, K. et al., "MEGA6: Molecular Evolutionary Genetics Analysis Version 6.0," Mol. Biol. Evol. 2013, 30, 12, 2725-2729.
Tenore, S. B. and Ferreira, P. R.A., "The Place of Protease Inhibitors in Antiretroviral Treatment," Braz. J. Infect. Dis. 2009, 13, 5, 371-374.
Varghese, V. et al., "Prototypical Recombinant Multi-Protease-Inhibitor-Resistant Infectious Molecular Clones of Human Immunodeficiency Virus Type 1," Antimicrob. Agents Chemother. 2013, 57, 9, 4290-4299.
Weber, I. T. et al., "Molecular mechanics analysis of drug-resistant mutants of HIV protease," Protein Eng. 1999, 12, 6, 469-474.
Agniswamy, J. et al., "HIV-1 Protease with 20 Mutations Exhibits Extreme Resistance to Clinical Inhibitors through Coordinated Structural Rearrangements," Biochemistry, vol. 51; 2819-2828 (2012).
Anderson, E. et al., "LAPACK Users' Guide," 3rd Edition; Society for Industrial and Applied Mathematics (SIAM): Philadelphia, PA, Table of Contents (1999).
Appadurai, R. and Senapati, S., "Dynamical Network of HIV-1 Protease Mutants Reveals the Mechanism of Drug Resistance and Unhindered Activity," Biochemistry, vol. 55, 1529-1540 (2016).
Bethell, R.; Scherer, J.; Witvrouw, M.; Paquet, A.; Coakley, E.; Hall, D. Phenotypic Protease Inhibitor Resistance and Cross-Resistance in the Clinic from 2006 to 2008 and Mutational Prevalences in HIV from Patients with Discordant Tipranavir and Darunavir Susceptibility Phenotypes. AIDS Res. Hum. Retroviruses 2012, 28, 1019-1024.
Chang, M. W. and Torbett, B. E., "Accessory Mutations Maintain Stability in Drug-Resistant HIV-1 Protease," Journal of Molecular Biology, vol. 410; 756-760 (2011).
Collins, J. R. et al., "Flap Opening in HIV-1 Protease Simulated by 'Activated' Molecular Dynamics," Structural Biology, vol. 4; No. 4; 334-338 (1995).
Condra, J. H. et al., "In vivo Emergence of HIV-1 Variants Resistant to Multiple Protease Inhibitors," Nature, vol. 374; 569-571 (1995).
De Meyer, S. et al., "Resistance Profile of Darunavir: Combined 24-Week Results from the Power Trials," AIDS Research and Human Retroviruses, vol. 24; No. 3; 379-388 (2008).
Erickson, J. W., "The Not-So-Great Escape," Nature Structural Biology, vol. 2; No. 7; 523-529 (1995).
Ghosh, A. K. et al., "Design of HIV Protease Inhibitors Targeting Protein Backbone: An Effective Strategy for Combating Drug Resistance," Accounts of Chemical Research, vol. 41; No. 1; 78-86 (2008).
Gulnik, S. V. et al., "Kinetic Characterization and Cross-Resistance Patterns of HIV-1 Protease Mutants Selected under Drug Pressure," Biochemistry, vol. 34; 9282-9287 (1995).
Hogg, R. V., Tanis, E. A., Zimmerman, D. L. Probability and Statistical Inference, 9th Edition; Pearson Higher Education: Upper Saddle River, NJ, 2015.
Jacobson, M. P. et al., "A Hierarchical Approach to All-Atom Protein Loop Prediction," Proteins: Structural, Function, and Bioinformatics, vol. 55; 351-367 (2004).
Jacobson, M. P.; Friesner, R. A.; Xiang, Z.; Honig, B. On the Role of the Crystal Environment in Determining Protein Side-Chain Conformations. J. Mol. Biol. 2002, 320, 597-608.
Muzammil, S. et al., "A Major Role for a Set of Non-Active Site Mutations in the Development of HIV-1 Protease Drug Resistance," Biochemistry, vol. 42; 631-638 (2003).
Ozen, A. et al., "Dynamics of Preferential Substrate Recognition in HIV-1 Protease: Redefining the Substrate Envelope," Journal of Molecular Biology, vol. 410, 726 744 (2011).

(56) References Cited

OTHER PUBLICATIONS

Shivakumar, D. et al., "Prediction of Absolute Solvation Free Energies Using Molecular Dynamics Free Energy Perturbation and the OPLS Force Field," Journal of Chemical Theory and Computation, vol. 6; 1509-1519 (2010).

Skalova, T. et al., "HIV-1 Protease Mutations and Inhibitor Modifications Monitored on a Series of Complexes. Structural Basis for the Effect of the A71v Mutation on the Active Site," Journal of Med. Chem., vol. 49; 5777-5784 (2006).

S.R. Desmond Molecular Dynamics System. D.E. Shaw Research, Maestro-Desmond Interoperability Tools, Table of Contents (2015).

Surleraux, D. L. N. G. et al., "Discovery and Selection of TMC114, a Next Generation HIV-1 Protease Inhibitor," J. Med. Chem., vol. 48; 1813-1822 (2005).

Swanstrom, R. and Erona, J., "Human Immunodeficiency Virus Type-1 Protease Inhibitors: Therapeutic Successes and Failures, Suppression and Resistance," Pharmacology & Therapeutics, vol. 86; 145-170 (2000).

Wang, Y. et al., "The Higher Barrier of Darunavir and Tipranavir Resistance for HIV-1 Protease," Biochemical and Biophysical Research Communications, vol. 412; 737-742 (2011).

Notification Concerning Transmittal of International Preliminary Report on Patentability for International Application No. PCT/US2018/043712, entitled: "Method for Probing at Least One Binding Site of a Protein," dated Jan. 28, 2020.

Moonsamy, Suri et al.: "Single Active Site Mutation Causes Serious Resistance of HIV Reverse Transcriptase to Lamivudine: Insight from Multiple Molecular Dynamics Simulations," Cell Biochemistry and Biophysics, Totowa, NJ, vol. 74, No. 1, (2015), pp. 35-48.

Karubiu, Wilson et al: "Compensatory Role of Double Mutation N348I/M184V on Nevirapine Binding Landscape: Insight from Molecular Dynamics Simulation", Protein Journal Kluwer Academic/Plenum Publishers, Dordrecht, NL, vol. 33, No. 5, (2014) pp. 432-446.

Karthick, V. et al.: "Computational Investigation of Drug-Resistant Mutant of M2 Proton Channel (S31N) Against Rimantadine", Cell Biochemistry and Biophysics, Totowa, NJ, vol. 70, No. 2, (2014), pp. 975-982.

Ragland, Debra A. et al.: "Drug Resistance Conferred by Mutations Outside the Active Site through Alterations in the Dynamic and Structural Ensemble of HIV-1 Protease", Journal of the American Chemical Society, vol. 136, No. 34, (2014), pp. 11956-11963.

Doherty, Kathleen M. et al.: "A multifaceted analysis of HIV-1 protease multidrug resistance phenotypes", BMC Bioinformatics, Biomed Central, London, GB, vol. 12, No. 1, (2011) p. 477.

Ragland, Debra A. et al.: "Elucidating the Interdependence of Drug Resistance from Combinations of Mutations", J. Chem Theory Comput. 2017, 13, 5671-5682.

Supplementary Search Report for EP 18 83 7901 dated Mar. 12, 2021.

\* cited by examiner

| Residue Position 1 | Residue Position 2 | p-value |
|---|---|---|
| 13 | 84 | 0.00146 |
| 32 | 84 | 0.00146 |
| 33 | 84 | 0.00146 |
| 46 | 84 | 0.00146 |
| 14 | 84 | 0.00466 |

| Residue Position | p-value |
|---|---|
| 84 | 0.0046 |
| 46 | 0.00759 |
| 13 | 0.0175 |
| 57 | 0.0307 |
| 35 | 0.0395 |

| Residue Position 1 | Residue Position 2 | p-value |
|---|---|---|
| 13 | 84 | 0.00146 |
| 32 | 84 | 0.00146 |
| 33 | 84 | 0.00146 |
| 46 | 84 | 0.00146 |
| 14 | 84 | 0.00466 |

SEQUENCE LISTING

<160> NUMBER OF SEQ ID NOS: 16

<210> SEQ ID NO 1
<211> LENGTH: 99
<212> TYPE: PRT

```
<213> ORGANISM: Artificial Sequence
<220> FEATURE:
<223> OTHER INFORMATION: SF-2 and NL4-3
<220> FEATURE:
<221> NAME/KEY: VARIANT
<222> LOCATION: 7
<223> OTHER INFORMATION: Xaa = Q or K
<220> FEATURE:
<221> NAME/KEY: VARIANT
<222> LOCATION: 10
<223> OTHER INFORMATION: Xaa = I or L
<220> FEATURE:
<221> NAME/KEY: VARIANT
<222> LOCATION: 13
<223> OTHER INFORMATION: Xaa = V or I
<220> FEATURE:
<221> NAME/KEY: VARIANT
<222> LOCATION: 14
<223> OTHER INFORMATION: Xaa = R or K
<220> FEATURE:
<221> NAME/KEY: VARIANT
<222> LOCATION: 32
<223> OTHER INFORMATION: Xaa = I or V
<220> FEATURE:
<221> NAME/KEY: VARIANT
<222> LOCATION: 33
<223> OTHER INFORMATION: Xaa = L or F
<220> FEATURE:
<221> NAME/KEY: VARIANT
<222> LOCATION: 36
<223> OTHER INFORMATION: Xaa = I or M
<220> FEATURE:
<221> NAME/KEY: VARIANT
<222> LOCATION: 37
<223> OTHER INFORMATION: Xaa = D or N
<220> FEATURE:
<221> NAME/KEY: VARIANT
<222> LOCATION: 41
<223> OTHER INFORMATION: Xaa = K or R
<220> FEATURE:
<221> NAME/KEY: VARIANT
<222> LOCATION: 46
<223> OTHER INFORMATION: Xaa = I or M
<220> FEATURE:
<221> NAME/KEY: VARIANT
<222> LOCATION: 47
<223> OTHER INFORMATION: Xaa = V or I
<220> FEATURE:
<221> NAME/KEY: VARIANT
<222> LOCATION: 54
<223> OTHER INFORMATION: Xaa = M or I
<220> FEATURE:
<221> NAME/KEY: VARIANT
<222> LOCATION: 57
<223> OTHER INFORMATION: Xaa = K or R
<220> FEATURE:
<221> NAME/KEY: VARIANT
<222> LOCATION: 62
<223> OTHER INFORMATION: Xaa = V or I
<220> FEATURE:
<221> NAME/KEY: VARIANT
<222> LOCATION: 63
<223> OTHER INFORMATION: Xaa = L or P
<220> FEATURE:
<221> NAME/KEY: VARIANT
<222> LOCATION: 64
<223> OTHER INFORMATION: Xaa = V or I
<220> FEATURE:
<221> NAME/KEY: VARIANT
<222> LOCATION: 71
<223> OTHER INFORMATION: Xaa = V or A
<220> FEATURE:
<221> NAME/KEY: VARIANT
<222> LOCATION: 82
<223> OTHER INFORMATION: Xaa = F or V or A
<220> FEATURE:
<221> NAME/KEY: VARIANT
<222> LOCATION: 84
<223> OTHER INFORMATION: Xaa = V or I
```

```
<220> FEATURE:
<221> NAME/KEY: VARIANT
<222> LOCATION: 89
<223> OTHER INFORMATION: Xaa = V or L
<220> FEATURE:
<221> NAME/KEY: VARIANT
<222> LOCATION: 90
<223> OTHER INFORMATION: Xaa = M or L

<400> SEQUENCE: 1

Pro Gln Ile Thr Leu Trp Xaa Arg Pro Xaa Val Thr Xaa Xaa Ile Gly
1               5                   10                  15

Gly Gln Leu Lys Glu Ala Leu Leu Asp Thr Gly Ala Asp Asp Thr Xaa
            20                  25                  30

Xaa Glu Glu Xaa Xaa Leu Pro Gly Xaa Trp Lys Pro Lys Xaa Xaa Gly
        35                  40                  45

Gly Ile Gly Gly Phe Xaa Lys Val Xaa Gln Tyr Asp Gln Xaa Xaa Xaa
    50                  55                  60

Glu Ile Cys Gly His Lys Xaa Ile Gly Thr Val Leu Val Gly Pro Thr
65                  70                  75                  80

Pro Xaa Asn Xaa Ile Gly Arg Asn Xaa Xaa Thr Gln Ile Gly Cys Thr
            85                  90                  95

Leu Asn Phe

<210> SEQ ID NO 2
<211> LENGTH: 99
<212> TYPE: PRT
<213> ORGANISM: Artificial Sequence
<220> FEATURE:
<223> OTHER INFORMATION: SF-2

<400> SEQUENCE: 2

Pro Gln Ile Thr Leu Trp Lys Arg Pro Leu Val Thr Ile Arg Ile Gly
1               5                   10                  15

Gly Gln Leu Lys Glu Ala Leu Leu Asp Thr Gly Ala Asp Asp Thr Val
            20                  25                  30

Leu Glu Glu Met Asn Leu Pro Gly Lys Trp Lys Pro Lys Met Ile Gly
        35                  40                  45

Gly Ile Gly Gly Phe Ile Lys Val Arg Gln Tyr Asp Gln Ile Pro Val
    50                  55                  60

Glu Ile Cys Gly His Lys Ala Ile Gly Thr Val Leu Val Gly Pro Thr
65                  70                  75                  80

Pro Val Asn Ile Ile Gly Arg Asn Leu Leu Thr Gln Ile Gly Cys Thr
            85                  90                  95

Leu Asn Phe

<210> SEQ ID NO 3
<211> LENGTH: 99
<212> TYPE: PRT
<213> ORGANISM: Artificial Sequence
<220> FEATURE:
<223> OTHER INFORMATION: NL4-3

<400> SEQUENCE: 3

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Asn Leu Pro Gly Arg Trp Lys Pro Lys Met Ile Gly
        35                  40                  45
```

```
Gly Ile Gly Gly Phe Ile Lys Val Arg Gln Tyr Asp Gln Ile Leu Ile
            50                  55                  60
Glu Ile Cys Gly His Lys Ala Ile Gly Thr Val Leu Val Gly Pro Thr
 65                  70                  75                  80
Pro Val Asn Ile Ile Gly Arg Asn Leu Leu Thr Gln Ile Gly Cys Thr
                85                  90                  95
Leu Asn Phe

<210> SEQ ID NO 4
<211> LENGTH: 99
<212> TYPE: PRT
<213> ORGANISM: Artificial Sequence
<220> FEATURE:
<223> OTHER INFORMATION: L76V

<400> SEQUENCE: 4

Pro Gln Ile Thr Leu Trp Lys Arg Pro Leu Val Thr Ile Arg Ile Gly
 1               5                  10                  15
Gly Gln Leu Lys Glu Ala Leu Leu Asp Thr Gly Ala Asp Asp Thr Val
                20                  25                  30
Leu Glu Glu Met Asn Leu Pro Gly Lys Trp Lys Pro Lys Met Ile Gly
            35                  40                  45
Gly Ile Gly Gly Phe Ile Lys Val Arg Gln Tyr Asp Gln Ile Pro Val
            50                  55                  60
Glu Ile Cys Gly His Lys Ala Ile Gly Thr Val Val Gly Pro Thr
 65                  70                  75                  80
Pro Val Asn Ile Ile Gly Arg Asn Leu Leu Thr Gln Ile Gly Cys Thr
                85                  90                  95
Leu Asn Phe

<210> SEQ ID NO 5
<211> LENGTH: 99
<212> TYPE: PRT
<213> ORGANISM: Artificial Sequence
<220> FEATURE:
<223> OTHER INFORMATION: L33F

<400> SEQUENCE: 5

Pro Gln Ile Thr Leu Trp Lys Arg Pro Leu Val Thr Ile Arg Ile Gly
 1               5                  10                  15
Gly Gln Leu Lys Glu Ala Leu Leu Asp Thr Gly Ala Asp Asp Thr Val
                20                  25                  30
Phe Glu Glu Met Asn Leu Pro Gly Lys Trp Lys Pro Lys Met Ile Gly
            35                  40                  45
Gly Ile Gly Gly Phe Ile Lys Val Arg Gln Tyr Asp Gln Ile Pro Val
            50                  55                  60
Glu Ile Cys Gly His Lys Ala Ile Gly Thr Val Leu Val Gly Pro Thr
 65                  70                  75                  80
Pro Val Asn Ile Ile Gly Arg Asn Leu Leu Thr Gln Ile Gly Cys Thr
                85                  90                  95
Leu Asn Phe

<210> SEQ ID NO 6
<211> LENGTH: 99
<212> TYPE: PRT
<213> ORGANISM: Artificial Sequence
<220> FEATURE:
<223> OTHER INFORMATION: V32I
```

<400> SEQUENCE: 6

```
Pro Gln Ile Thr Leu Trp Lys Arg Pro Leu Val Thr Ile Arg Ile Gly
1               5                   10                  15

Gly Gln Leu Lys Glu Ala Leu Leu Asp Thr Gly Ala Asp Asp Thr Ile
            20                  25                  30

Leu Glu Glu Met Asn Leu Pro Gly Lys Trp Lys Pro Lys Met Ile Gly
        35                  40                  45

Gly Ile Gly Gly Phe Ile Lys Val Arg Gln Tyr Asp Gln Ile Pro Val
    50                  55                  60

Glu Ile Cys Gly His Lys Ala Ile Gly Thr Val Leu Val Gly Pro Thr
65                  70                  75                  80

Pro Val Asn Ile Ile Gly Arg Asn Leu Leu Thr Gln Ile Gly Cys Thr
                85                  90                  95

Leu Asn Phe
```

<210> SEQ ID NO 7
<211> LENGTH: 99
<212> TYPE: PRT
<213> ORGANISM: Artificial Sequence
<220> FEATURE:
<223> OTHER INFORMATION: DM

<400> SEQUENCE: 7

```
Pro Gln Ile Thr Leu Trp Lys Arg Pro Leu Val Thr Ile Arg Ile Gly
1               5                   10                  15

Gly Gln Leu Lys Glu Ala Leu Leu Asp Thr Gly Ala Asp Asp Thr Ile
            20                  25                  30

Phe Glu Glu Met Asn Leu Pro Gly Lys Trp Lys Pro Lys Met Ile Gly
        35                  40                  45

Gly Ile Gly Gly Phe Ile Lys Val Arg Gln Tyr Asp Gln Ile Pro Val
    50                  55                  60

Glu Ile Cys Gly His Lys Ala Ile Gly Thr Val Leu Val Gly Pro Thr
65                  70                  75                  80

Pro Val Asn Ile Ile Gly Arg Asn Leu Leu Thr Gln Ile Gly Cys Thr
                85                  90                  95

Leu Asn Phe
```

<210> SEQ ID NO 8
<211> LENGTH: 99
<212> TYPE: PRT
<213> ORGANISM: Artificial Sequence
<220> FEATURE:
<223> OTHER INFORMATION: I93L

<400> SEQUENCE: 8

```
Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Asn Leu Pro Gly Arg Trp Lys Pro Lys Met Ile Gly
        35                  40                  45

Gly Ile Gly Gly Phe Ile Lys Val Arg Gln Tyr Asp Gln Ile Leu Ile
    50                  55                  60

Glu Ile Cys Gly His Lys Ala Ile Gly Thr Val Leu Val Gly Pro Thr
65                  70                  75                  80

Pro Val Asn Ile Ile Gly Arg Asn Leu Leu Thr Gln Leu Gly Cys Thr
```

85                  90                  95

Leu Asn Phe

<210> SEQ ID NO 9
<211> LENGTH: 99
<212> TYPE: PRT
<213> ORGANISM: Artificial Sequence
<220> FEATURE:
<223> OTHER INFORMATION: I84V

<400> SEQUENCE: 9

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Asn Leu Pro Gly Arg Trp Lys Pro Lys Met Ile Gly
        35                  40                  45

Gly Ile Gly Gly Phe Ile Lys Val Arg Gln Tyr Asp Gln Ile Leu Ile
    50                  55                  60

Glu Ile Cys Gly His Lys Ala Ile Gly Thr Val Leu Val Gly Pro Thr
65                  70                  75                  80

Pro Val Asn Val Ile Gly Arg Asn Leu Leu Thr Gln Ile Gly Cys Thr
                85                  90                  95

Leu Asn Phe

<210> SEQ ID NO 10
<211> LENGTH: 99
<212> TYPE: PRT
<213> ORGANISM: Artificial Sequence
<220> FEATURE:
<223> OTHER INFORMATION: DRVr8

<400> SEQUENCE: 10

Pro Gln Ile Thr Leu Trp Gln Arg Pro Leu Val Thr Val Lys Ile Glu
1               5                   10                  15

Gly Gln Leu Lys Glu Ala Leu Leu Asp Thr Gly Ala Asp Asp Thr Ile
            20                  25                  30

Phe Glu Glu Met Asn Leu Pro Gly Arg Trp Lys Pro Ile Ile Ile Gly
        35                  40                  45

Gly Ile Gly Gly Phe Ile Lys Val Arg Gln Tyr Asp Gln Ile Leu Ile
    50                  55                  60

Glu Ile Cys Gly His Lys Ala Ile Gly Thr Val Leu Val Gly Pro Thr
65                  70                  75                  80

Pro Phe Asn Val Ile Gly Arg Asn Leu Leu Thr Gln Ile Gly Cys Thr
                85                  90                  95

Leu Asn Phe

<210> SEQ ID NO 11
<211> LENGTH: 99
<212> TYPE: PRT
<213> ORGANISM: Artificial Sequence
<220> FEATURE:
<223> OTHER INFORMATION: DRVr10

<400> SEQUENCE: 11

Pro Gln Ile Thr Leu Trp Gln Arg Pro Leu Val Thr Val Lys Ile Glu
1               5                   10                  15

Gly Gln Leu Lys Glu Ala Leu Leu Asp Thr Gly Ala Asp Asp Thr Ile
            20                  25                  30

```
Phe Glu Glu Met Asn Leu Pro Gly Arg Trp Lys Pro Ile Ile Ile Gly
             35                  40                  45

Gly Ile Gly Gly Phe Ile Lys Val Arg Gln Tyr Asp Gln Ile Leu Ile
         50                  55                  60

Glu Ile Cys Gly His Lys Val Ile Gly Thr Val Val Gly Pro Thr
 65                  70                  75                  80

Pro Phe Asn Val Ile Gly Arg Asn Leu Leu Thr Gln Ile Gly Cys Thr
                 85                  90                  95

Leu Asn Phe

<210> SEQ ID NO 12
<211> LENGTH: 99
<212> TYPE: PRT
<213> ORGANISM: Artificial Sequence
<220> FEATURE:
<223> OTHER INFORMATION: ATA21

<400> SEQUENCE: 12

Pro Gln Ile Thr Leu Trp Lys Arg Pro Phe Ile Thr Val Lys Ile Gly
 1               5                  10                  15

Gly Gln Gln Met Glu Ala Leu Leu Asp Thr Gly Ala Asp Asp Thr Ile
             20                  25                  30

Phe Glu Ala Ile Asn Leu Pro Gly Arg Trp Lys Pro Lys Ile Val Gly
             35                  40                  45

Gly Ile Gly Gly Phe Met Lys Val Lys Gln Tyr Asp Gln Val Pro Val
         50                  55                  60

Glu Ile Cys Gly His Lys Ala Ile Thr Ala Leu Val Gly Pro Thr
 65                  70                  75                  80

Pro Val Asn Val Ile Gly Arg Asn Val Met Thr Gln Ile Gly Cys Thr
                 85                  90                  95

Leu Asn Phe

<210> SEQ ID NO 13
<211> LENGTH: 99
<212> TYPE: PRT
<213> ORGANISM: Artificial Sequence
<220> FEATURE:
<223> OTHER INFORMATION: KY26

<400> SEQUENCE: 13

Pro Gln Ile Thr Leu Trp Lys Arg Pro Val Val Val Lys Val Gly
 1               5                  10                  15

Gly Gln Leu Met Glu Ala Leu Leu Asp Thr Gly Ala Asp Asp Thr Ile
             20                  25                  30

Phe Glu Glu Met Asn Leu Pro Gly Arg Trp Thr Pro Lys Ile Val Gly
             35                  40                  45

Gly Ile Gly Gly Phe Met Lys Val Arg Gln Tyr Glu Asn Val Pro Ile
         50                  55                  60

Glu Ile Tyr Gly Lys Lys Ile Leu Ser Thr Val Leu Ile Gly Pro Thr
 65                  70                  75                  80

Pro Ala Asn Ile Ile Gly Arg Asn Val Met Thr Gln Ile Gly Cys Thr
                 85                  90                  95

Leu Asn Phe

<210> SEQ ID NO 14
<211> LENGTH: 99
<212> TYPE: PRT
```

<213> ORGANISM: Artificial Sequence
<220> FEATURE:
<223> OTHER INFORMATION: SLK19

<400> SEQUENCE: 14

Pro Gln Ile Thr Leu Trp Lys Arg Pro Ile Leu Thr Val Arg Ile Gly
1               5                   10                  15

Gly Gln Leu Lys Glu Val Leu Leu Asp Thr Gly Ala Asp Asp Thr Val
            20                  25                  30

Leu Glu Asp Ile Asp Leu Pro Gly Arg Trp Lys Pro Lys Met Ile Met
        35                  40                  45

Gly Ile Gly Gly Leu Val Lys Val Arg Gln Tyr Asp Gln Val Pro Ile
    50                  55                  60

Glu Ile Cys Gly His Lys Val Ile Gly Ser Val Leu Val Gly Pro Thr
65                  70                  75                  80

Pro Ala Asn Ile Val Gly Arg Asn Leu Leu Ser Lys Ile Gly Cys Thr
                85                  90                  95

Leu Asn Phe

<210> SEQ ID NO 15
<211> LENGTH: 99
<212> TYPE: PRT
<213> ORGANISM: Artificial Sequence
<220> FEATURE:
<223> OTHER INFORMATION: VEG23

<400> SEQUENCE: 15

Pro Gln Ile Thr Leu Trp Lys Arg Pro Ile Ile Lys Val Lys Ile Gly
1               5                   10                  15

Gly Gln Leu Val Glu Ala Leu Leu Asp Thr Gly Ala Asp Asp Thr Ile
            20                  25                  30

Phe Glu Gly Ile Asp Leu Pro Gly Arg Trp Lys Pro Lys Ile Val Gly
        35                  40                  45

Gly Ile Gly Gly Phe Met Lys Val Lys Glu Tyr Asp Gln Ile Pro Val
    50                  55                  60

Glu Val Cys Gly His Lys Val Ile Ser Thr Val Leu Val Gly Pro Thr
65                  70                  75                  80

Pro Val Asn Val Ile Gly Arg Asn Val Met Thr Gln Ile Gly Cys Thr
                85                  90                  95

Leu Asn Phe

<210> SEQ ID NO 16
<211> LENGTH: 99
<212> TYPE: PRT
<213> ORGANISM: Artificial Sequence
<220> FEATURE:
<223> OTHER INFORMATION: VSL23

<400> SEQUENCE: 16

Pro Gln Ile Thr Leu Trp Lys Arg Pro Ile Val Thr Ile Lys Ile Gly
1               5                   10                  15

Gly Gln Leu Arg Glu Ala Leu Leu Asp Thr Gly Ala Asp Asp Thr Val
            20                  25                  30

Phe Thr Asp Ile Asp Leu Pro Gly Arg Trp Thr Pro Lys Ile Ile Val
        35                  40                  45

Gly Val Gly Gly Phe Ser Lys Val Lys Gln Tyr Asp Gln Val Pro Ile
    50                  55                  60

Glu Ile Cys Gly His Lys Val Val Gly Thr Val Leu Ile Gly Pro Thr

```
                65                  70                  75                  80
Pro Ala Asn Ile Val Gly Arg Asn Leu Leu Thr Gln Leu Gly Cys Thr
                        85                  90                  95
Leu Asn Phe
```

METHOD FOR PROBING AT LEAST ONE BINDING SITE OF A PROTEIN

RELATED APPLICATION

This application claims the benefit of U.S. Provisional Application No. 62/536,930, filed on Jul. 25, 2017. The entire teachings of the above application are incorporated herein by reference.

GOVERNMENT SUPPORT

This invention was made with government support under Grant Numbers GM109767 and GM111101 awarded by the National Institutes of Health. The government has certain rights in the invention.

INCORPORATION BY REFERENCE OF MATERIAL IN ASCII TEXT FILE

This application incorporates by reference the Sequence Listing contained in the following ASCII text file being submitted concurrently herewith:
a) File name: 54391000001_SEQUENCELISTING.txt; created Jul. 24, 2018, 16 KB in size.

BACKGROUND

While structure-based drug design (SBDD) has accelerated rational design of inhibitors for many key targets, including the use of free energy perturbation (FEP) to predict the relative binding affinity of similar inhibitors, many shortcomings still exist. Protein inhibitor binding is dynamic. However, dynamics is generally are not incorporated in drug design. Molecular dynamics provides information that typically is not applied systematically to a series of targets and/or ligands. As a consequence, the impact of changes in a drug target that occur remote from an active site are not incorporated in drug design, but nonetheless impact the binding affinity of inhibitors. Therefore, such methods generally are not able to accurately predict the coupled changes within a ligand that dictate not only the interdependency of molecular recognition and specificity that is necessary to avoid drug resistance, but also are required for inhibitor design.

Therefore, a need exists for a method for probing at least one binding site of protein, or macromolecular target, that overcomes or minimizes the above referenced problems.

SUMMARY

The invention generally is directed to a method for probing at least one binding site of protein, or drug target.

In one embodiment, the method includes calculating a set of molecular dynamics trajectories of a protein-ligand complex family, wherein the protein-ligand complex family includes a plurality of members that vary in the structure of the protein, the ligand, or both. At least one first script is applied to the molecular dynamic trajectories to form a set of tensors, wherein each tensor is a set of physical properties for a member of the protein-ligand complex family. At least one second script is applied to the set of tensors to integrate the set of sensors with experimental binding data corresponding to each member of the protein-ligand complex family to form a primary image of the binding site, thereby probing the binding site of the protein.

This invention has many advantages. For example, interdependent changes of molecular recognition and specificity can be characterized, such as by developing physical fingerprints from parallel molecular dynamic trajectories of ligand-target complexes and by employing machine learning to deduce specific alterations. Examples of such specific alterations that can be identified by the method of the invention include the impact of changes in sequence and a target, such as within the active site or binding site, and remote from the active site or binding site. Other changes include those in the ligand, wherein a series of ligands are evaluated to assess advantageous binding affinity. Data generated by the method of the invention include subsites where changes in the inhibitor optimize specificity and affinity, thereby assisting in the development of ligands that will, for example, increase specificity or potency to a target, and avoid drug resistance, such as by identifying ligands that better fit within a substrate envelope, or avoid the influence of pivotal remote changes that contribute to drug resistance. Additionally, the methods of the invention can be utilized for studying macromolecular interactions, such as one or more complexes of DNA-protein DNA-DNA, DNA-RNA, protein-RNA, carbohydrate-protein, ligand-DNA, ligand-RNA, macromolecule, lipid protein, protein-protein, and viral assembly interactions, thereby assisting in the development of better interventions for treating disease, such as neutralizing antibodies for protein antigen, better ligands, competitive inhibitors for malfunctioning enzymes, making better viral vectors for research and Gene therapy applications; making better enzymes or proteins for manufacturing applications, and for treating human disease via enzyme/protein replacement therapy and therapeutic antibodies.

BRIEF DESCRIPTION OF THE DRAWINGS

FIG. 2A is a sequence alignment of a panel of fifteen HIV-1 protease variants. Mutations are highlighted as compared to the SF-2 WT protease (PDB accession code 1T3R; PDB code 2HB4 denotes NL4-3 WT).

FIG. 2B is a sequence identity matrix for 15 HIV-1 protease variants of FIG. 1A. Values are colored from blue to red for high to low % identities.

Figure 1:
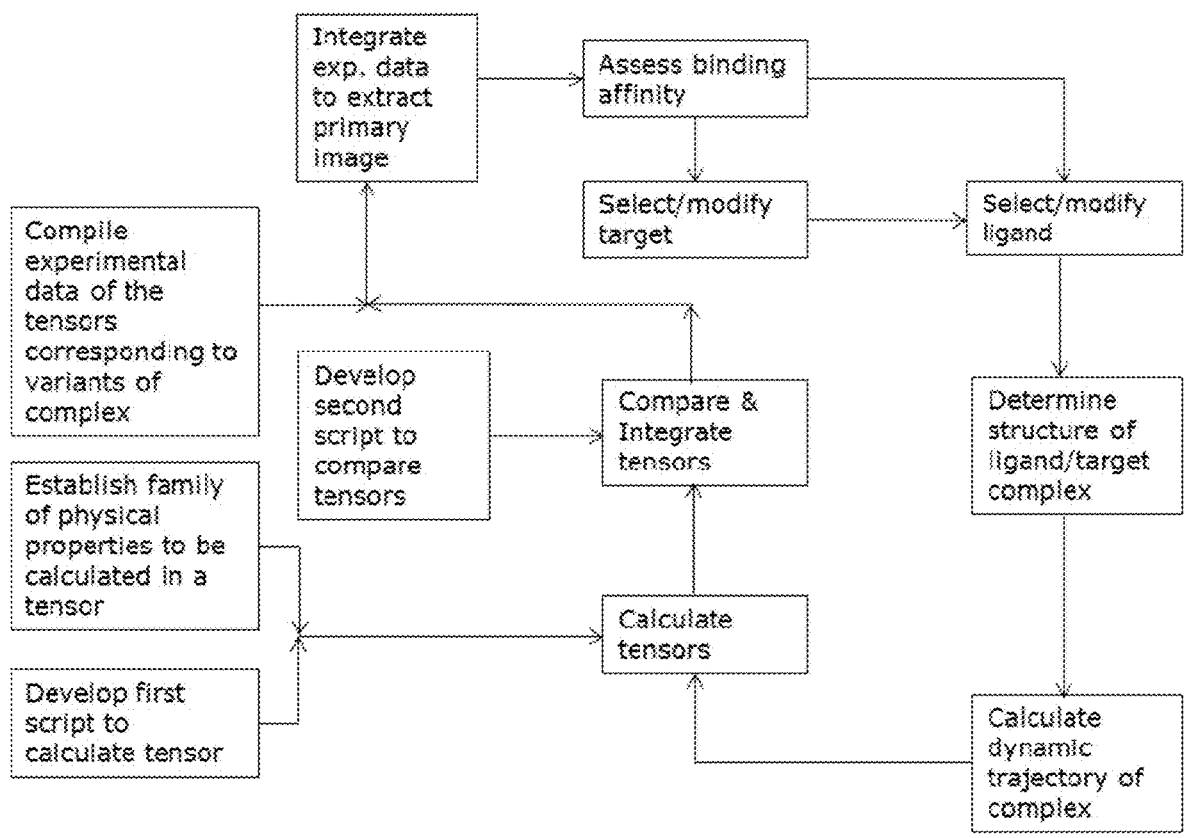
FIG. 1 is a schematic representation of one embodiment of the method of the invention.

In one embodiment the calculation of the molecular dynamic trajectories incorporates binding affinity of the protein ligand complex. In still another embodiment, the calculation of the molecular dynamic trajectories further incorporates a determination of at least one physical feature of the protein ligand complex. In a specific embodiment, the at least one physical feature of the protein-ligand complex includes at least one member of the group consisting of: hydrogen bonding; van der Waals force; water structure; correlated motions; internal distances; and at least one of root mean square deviation (RMSD) and root mean square fluctuation (RMSF) of atoms of the protein or ligand, or both the protein and ligand of the protein-ligand complex.

In one embodiment, the hydrogen bonding is of the protein of the protein-ligand complex. In another embodiment, the hydrogen bonding is of the ligand of the protein-ligand protein complex. In yet another embodiment, the hydrogen bonding is of both the protein and the ligand of the protein-ligand complex In another embodiment, the van der Waals interaction is of the protein of the protein-ligand complex. In still another embodiment, the van der Waals interaction is of the ligand of the protein-ligand complex. In yet another embodiment, the van der Walls interaction is of both the protein and the ligand of the protein-ligand complex.

In one embodiment, the water structure is of the protein of the protein-ligand complex. In another embodiment, the water structure is of the ligand of the protein-ligand complex. In yet another embodiment, the water structure is of the protein and the ligand of the protein-ligand complex. Examples of water structure are described, for example in Leidner F., Kurt Yilmaz, N., Paulsen J., Muller, Y. A, Schiffer, C. A. "Hydration Structure and Dynamics of Inhibitor-Bound HIV-1 Protease." *J. Chem. Theory Comput.* 2018 May 8; 14(5):2784-2796. doi: 10.1021/acs.jctc.8b00097.

In one embodiment, the correlated motion includes mutual information and correlation coefficient matrices, such as are known in the art. Examples of matrices of correlation coefficients are described, for example, in Soumana, D. I., Kurt-Yilmaz, N., Ali A., Prachanronarong, K. L., and Schiffer, C. A., "Molecular and Dynamic Mechanism Underlying Drug Resistance in Genotype 3 Hepatitis C NS3/4A Protease," *J. Am. Chem. Soc.* 138, 11850-11859 (2016), and Paulson, J. L., Leidner, F., Ragland, D. A., Kurt-Yilmaz, N., and Schiffer, C. A., "Interdependence of Inhibitor Recognition in HIV-1 Protease," *J. of Chem. Theory and Comput.* 13, 2300-2309 (2017), the relevant teachings of all of which are incorporated by reference in their entirety.

In a particular embodiment, the physical property is in the form of a distance difference plot of internal distances, wherein, for example, distance difference matrices are generated for each inhibitor-mutant pair to reveal structural changes relative to that inhibitor bound to a wild-type (WT) protease, as described, for example, in Prabu-Jeyabalan, M., Nalivaika, E. A., Romano, K., and Schiffer, C. A., "Mechanism of substrate recognition by drug-resistant human immunodeficiency virus type I protease variants revealed by novel structural intermediates," *J. Virol.*, 80, 3607-3616, doi: 10.1128/jvi.80.7.3607-3616.2006 (2006), the relevant teachings of all of which are incorporated by reference in their entirety. Suitable distance-different matrices can be generated by methods known to those skilled in the art.

In still another embodiment, at least one of the root mean square deviation (RMSD) and the root-mean-square fluctuation (RMSF) is of the protein of the protein-ligand complex. In another embodiment, at least one of the root mean square deviation and the root mean square fluctuation is of the ligand of the protein-ligand complex. In still another embodiment, at least one of the root mean square deviation and the root mean square fluctuation is of the protein and the ligand and the protein-ligand complex.

In another embodiment, the protein-ligand complex family includes a plurality of ligands, each of which is bound to the protein, wherein the protein-ligand complex family includes a plurality of protein-ligand complex pairs. In another embodiment, the protein-ligand complex family further includes a plurality of variants of the protein, each of which is bound to the protein, wherein the protein-ligand complex family includes a plurality of protein-ligand pairs. Examples of such techniques are also described in Özen A., Lin K. H., Kurt Yilmaz N., Schiffer C. A. Structural basis and distal effects of Gag substrate coevolution in drug resistance to HIV-1 protease. *Proc. Natl. Acad. Sci. U.S.A.* 2014 Nov. 11; 111(45):15993-8 and Ozen A, Sherman W, Schiffer C. A., "Improving the Resistance Profile of Hepatitis C NS3/4A Inhibitors: Dynamic Substrate Envelope Guided Design," *J. Chem. Theory Comput.* 2013 Dec. 10; 9(12):5693-5705.

In one embodiment, to calculate intermolecular van der Waals (VdW) interaction energies, crystal structures can be prepared. Hydrogen atoms can be added, protein sequences determined, and structures minimized. Subsequently, force field parameters can be assigned using an atomic force field for macromolecular interactions. Interaction energies between the inhibitor and protease can be estimated using a simplified Lennard-Jones potential, as is known in the art. For each protease residue, the change in van der Waals interactions relative to the wild-type or primary complex can be calculated for the mutant structures. Examples of such techniques are also described in Ragland D. A., Nalivaika, E. A., Nalam, M. N. L., Prachanronarong, K. L., Cao, H., Bandaranayake, R. M., Cai, Y., Kurt Yilmaz, N., and Schiffer, C. A., "Drug-Resistance Conferred by Mutations Outside the Active Site Through Alterations in the Dynamic and Structural Ensemble of HIV-1 Protease," *J. Am. Chem. Soc.*, 136, 11956-11963 (2014); and Paulson, J. L., Leidner, R., Kurt Yilmaz, N., "Interdependence of Inhibitor Recognition of HIV-1 Protease," *J. of Chem. Theory Comput.*, 13, 2300-2309 (2017), the relevant teachings of all of which are incorporated by reference in their entirety.

In one embodiment, the protein-ligand complex family includes a plurality of ligands, each of which is bound to the protein, wherein the protein-ligand complex family includes a plurality of protein-ligand complex pairs. In another embodiment, the protein-ligand complex family includes a plurality of variants of a protein, each of which is bound to the protein, wherein the protein-ligand complex family includes a plurality of protein-ligand complex pairs.

At least one first script is applied to the molecular dynamic trajectories to form a set of tensors, where each tensor is a set of physical properties for a member of the protein-ligand complex family. In one embodiment, at least one first script is applied to each protein-ligand complex pair of the protein-ligand complex family, whereby a tensor is formed for each protein-ligand complex pair of the protein-ligand complex family.

At least one second script is applied to the set of tensors to integrate the set of tensors with experimental binding data corresponding to each member of the protein-ligand complex family to form a primary image of the binding site, thereby probing the binding site of the protein. In one specific embodiment, applying at least one second script to the set of tensors includes at least one member of the group consisting of: comparative structural analysis among the protein-ligand complex pairs; identification of effective changes in amino acid sequence of the protein as occurs in drug resistance of a single target or between similar enzymes to avoid off target effects; and identification of effective changes to retain potency and/or specificity An effective change is reflected in the changes in one or more of the physical characteristics i.e., hydrogen bonding; van der Waals interaction; water structure; correlated motion; internal distances; and at least one of root mean square deviation and root mean square fluctuation of atoms in the binding affinity between the protein and ligand of each protein-ligand pair of each tensor. In another specific embodiment, the comparative structural analysis includes a comparison of at least one of the group consisting of: hydrogen bonding; van der Waals force; water structure; correlated motion; internal distances; and at least one of root mean square deviation and root mean square fluctuation of atoms of the protein, or ligand, or both the protein and ligand of the protein-ligand complex.

The following is an exemplification of the method of the invention, and is not intended to be limiting in any way.

EXEMPLIFICATION

A description of example embodiments follows.

HIV-1 protease is responsible for the cleavage of 12 non-homologous sites within the Gag and Gag-Pro-Pol polyproteins in the viral genome. Under the selective pressure of protease inhibition, the virus evolves mutations within (primary) and outside of (secondary) the active site allowing the protease to process substrates while simultaneously countering inhibition. The primary protease mutations impede inhibitor binding directly, while the secondary mutations are considered accessory mutations that compensate for a loss in fitness.

Below is a demonstration that mutations distal to the active site, regardless of context, can play an interdependent role in drug resistance. Eigenvalue decomposition was applied to collections of hydrogen bonding and van der Waals interactions from a series of molecular dynamics simulations of 15 diverse HIV-1 protease variants. Sites in the protease where amino acid substitutions lead to perturbations in non-bonded interactions with DRV and/or the hydrogen-bonding network of the protease itself were identified, thereby delineating the significant contributions of accessory mutations to resistance.

I. Introduction

Darunavir (DRV) is a highly potent protease inhibitor (PI) used in the treatment of patients infected with HIV-1. Unlike first generation PIs, DRV is able to withstand many mutations both within and outside of the protein's active site.[1-2] Due to a high barrier to resistance, single mutations do not individually cause significant DRV resistance, and substitutions responsible for cross-resistance to other PIs are still fairly susceptible to DRV inhibition.[3] Contributing factors to DRV's high genetic barrier to resistance include the tight binding affinity ($K_d$=4.5×10$^{-12}$ M),[4] extensive hydrogen bonding with several active site backbone atoms,[5] favorable hydrophobic contacts within the active site and a good fit within the substrate envelope.[6] However, even with all these key attributes the protease is still able to develop complex mutational patterns that facilitate evasion of DRV inhibition. Previous studies[7] have demonstrated an interdependence among specific amino acid substitutions that together result in resistance.

In such complex mutational patterns, active site mutations physically alter inhibitor binding and are, therefore, readily identified. However, the role of mutations beyond the active site is more difficult to characterize. For instance, the DRV resistance-associated mutations I84V, I50V, V32I and I47V all lie in positions where the inhibitor atoms protrude beyond the substrate envelope at the active site.[8] In clinical trials of DRV, however, several non-active site (secondary or accessory) mutations are selected for at positions 11, 33, 54, 73, 76, 85, and 89 among others,[9-10] and the role of these mutations in DRV resistance is not understood. The widely accepted notion is that accessory mutations have the sole purpose of balancing the destabilizing effects of primary active site mutations.[11] Studying the mutational tolerance of the protease using an empirical scoring function indicated that distal mutations could be beneficial not only via stabilizing monomeric fold dimerization but interactions with the substrate as well.[12] However, the direct role of accessory mutations in drug resistance has not been extensively probed[13-16] and even less well known are which specific variable positions outside the active site play a role in resistance.[7] Thus, while most mutations within the active site that arise to DRV are readily explained by the substrate envelope hypothesis, without a similar framework, evaluating the role of other mutations is not straightforward.

Previously, several single mutations and one double mutant variant of HIV-1 protease[16] were examined to gauge how secondary mutations away from the active site could play a role in protease inhibitor susceptibility. These mutations included V32I, located at the periphery of the active site, and a combination of V32I/L33F. Also, the distal DRV resistance associated mutation L76V and the non-DRV resistance associated mutation L90M were examined. Investigation of the crystal structures and molecular dynamics simulations of these variants bound to DRV showed that while these distal mutations alone do not drive significant levels of resistance, they were all able to perturb the network of hydrogen bonds within the protein, thereby propagating the effect to the protease active site causing slight loss of affinity. This network model provided a general understanding as to how mutation of residues may communicate with one another and why some co-mutant relationships may be synergistic or redundant.

The method of the invention was employed to characterize the role of mutations both near and distal from the active site in complex combinatorial backgrounds of a set of protease variants, and to make a comparison to the wild-type (WT) and single/double site mutants examined previously. Specifically, which variable positions in the protease are most relevant for resistance were determined, given the complex sequence variations observed among heavily mutated variants. Several DRV-resistant protease variants were selected from viral passaging experiments as well as patient-derived sequences from the HIV Drug Resistance Database.[18]

Figures 2A, 2B:
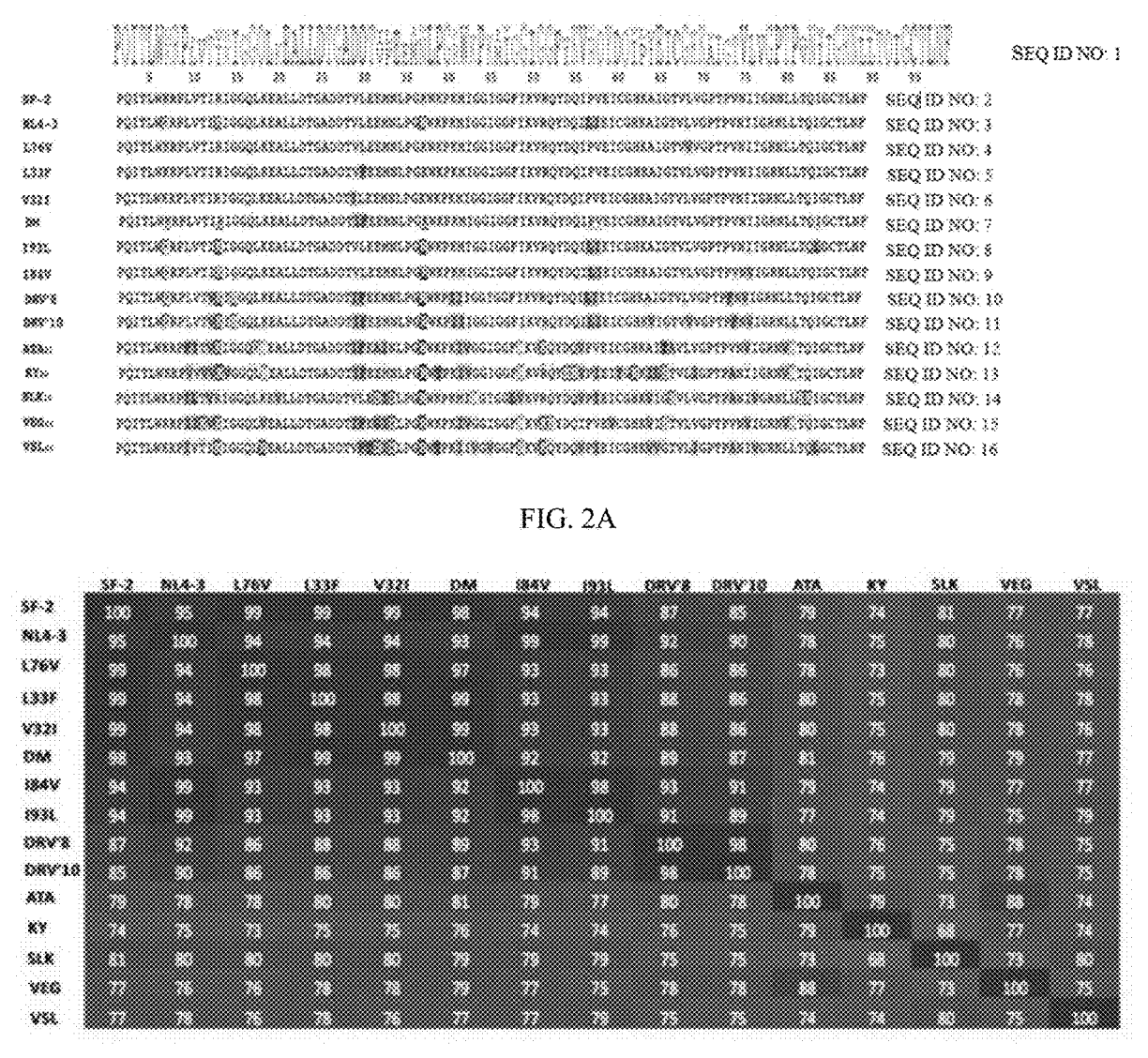
Figure 3:
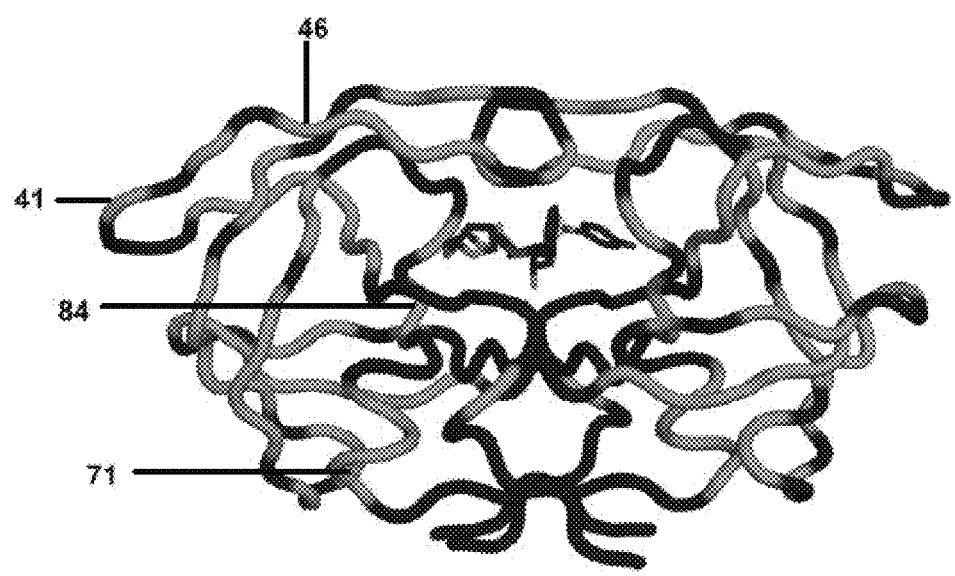
FIG. 3 is a protease structure mapped in blue with all 50 sequence substitutions within the panel highlighted in green; protease inhibitor DRV is shown in the active site.
Figure 4:
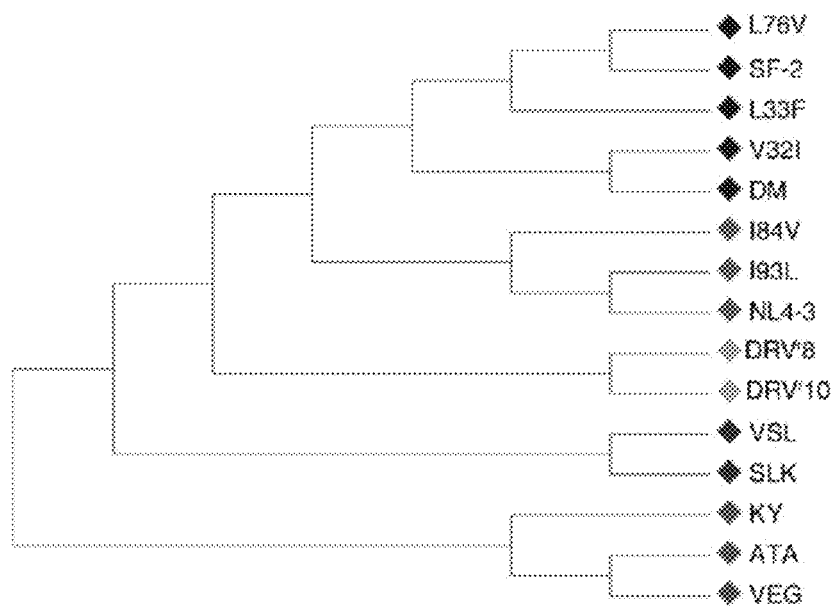
FIG. 4 is a neighbor-joining phylogenetic tree of all 15 protease variants. Colored annotations denote sequence similarity among variants.
Figure 5A:
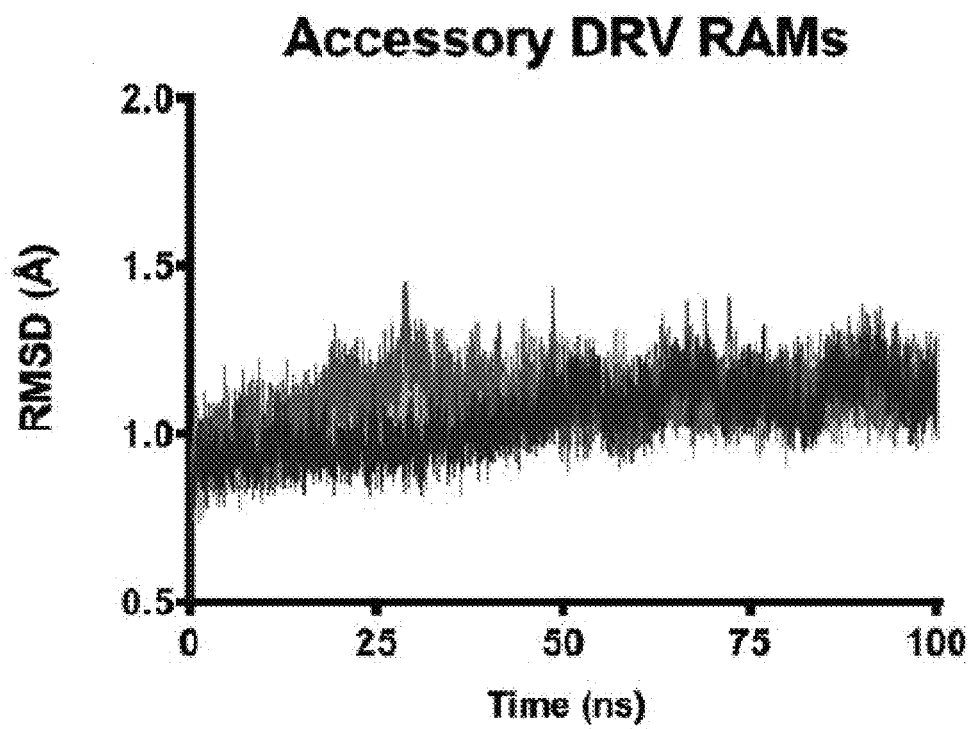
FIG. 5A is a plot of root mean square deviation (RMSD) values for MD simulations of HIV-1 protease variants for DRV accessory RAMs L76V, V32I, L33F, and V32I+L33F compared to SF-2 WT.
Figure 5B:
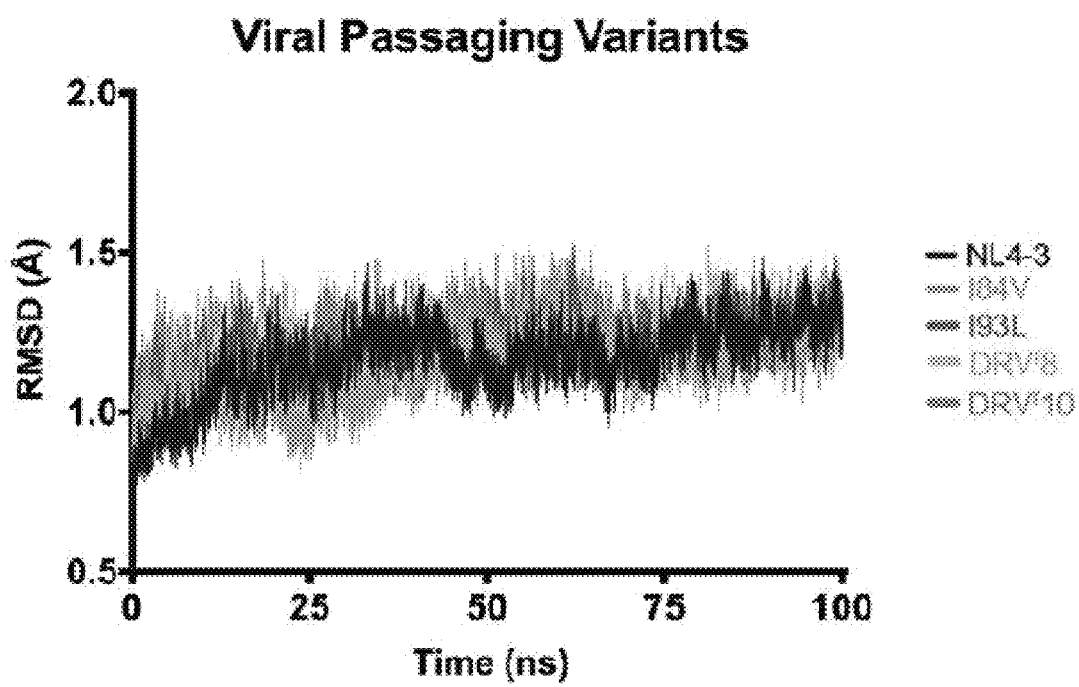
FIG. 5B is a plot of RMSD values for the MD simulation of FIG. 5A for viral passaging variants I84V, I93L, DRV''8 and DRV''10 compared to NL4-3 WT.
Figure 5C:
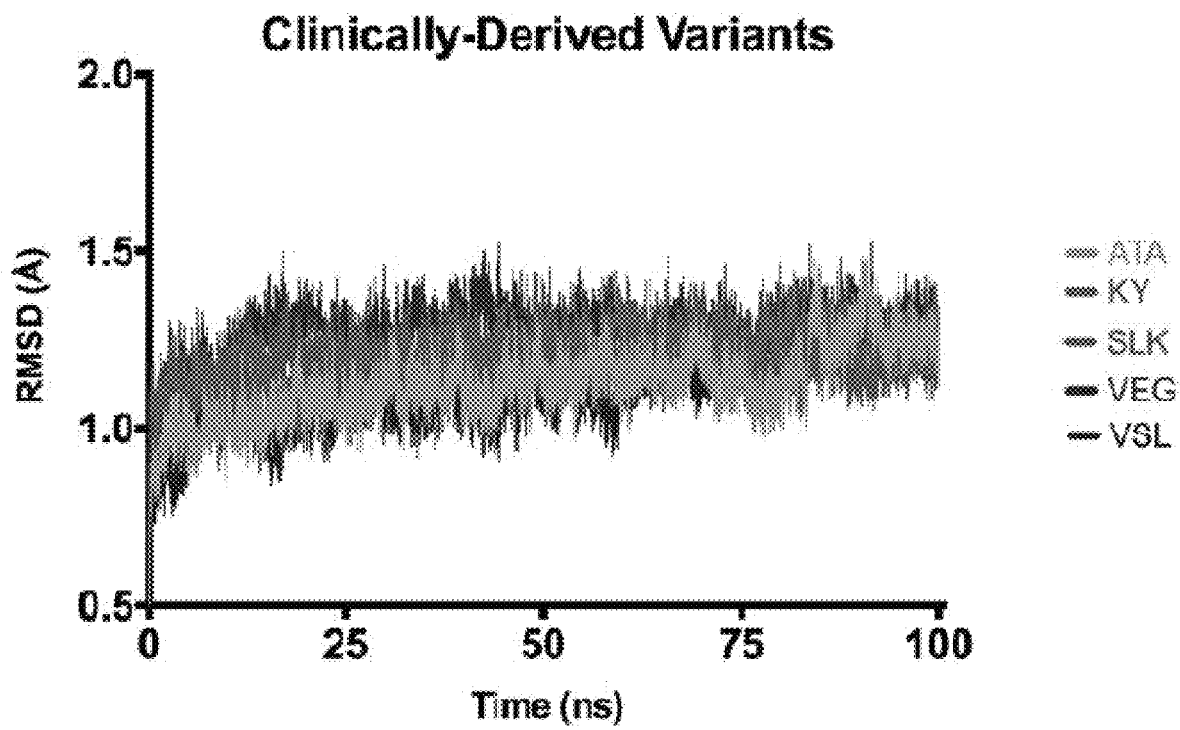
FIG. 5C is a plot of RMSD values for the MD simulation of FIGS. 5A and 5B for clinically-derived variants compared to SF-2 WT.

In one specific embodiment, a set of molecular dynamic trajectories are calculated, according to the method of the invention on a panel of 15 protease variants (SF-2 and NL4-3 wild-types and 13 other variants) all bound to DRV, all of which are shown in FIGS. 2-4, by conducting a series of molecular dynamics (MD) simulations tracked through root mean square deviations (RMSD) FIG. 5.

Figure 6:
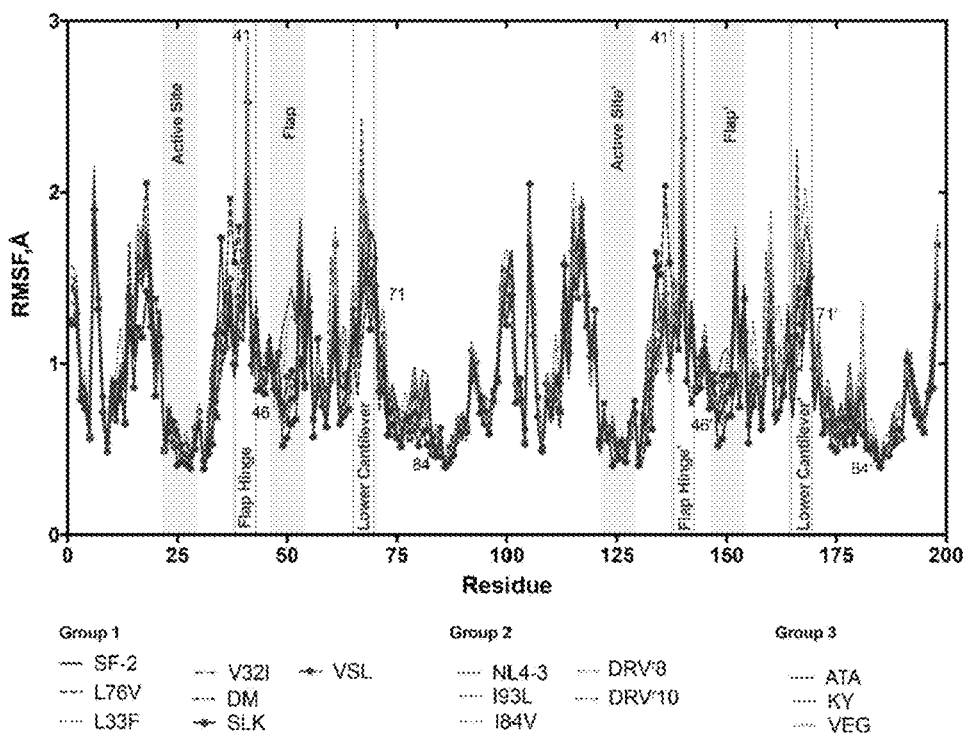
FIG. 6 is a plot of protease dynamics indicative of resistance including per-residue RMSF values for all 15 protease variants plotted in three groups, as defined by the clustering of the hierarchical dendrogram.

At least one script was applied to the molecular dynamic trajectories to form a set of tensors by analyses of root mean square fluctuations (RMSF). It was found that sequence similarity alone may be indicative of backbone dynamics in the variants. In addition, mean hydrogen bond occupancies (both intra-protease and DRV-protease) were collected from these trajectories, along with mean per-residue DRV-protease van der Waals energies, all of which are shown in FIGS. 6-8.

Figure 7:
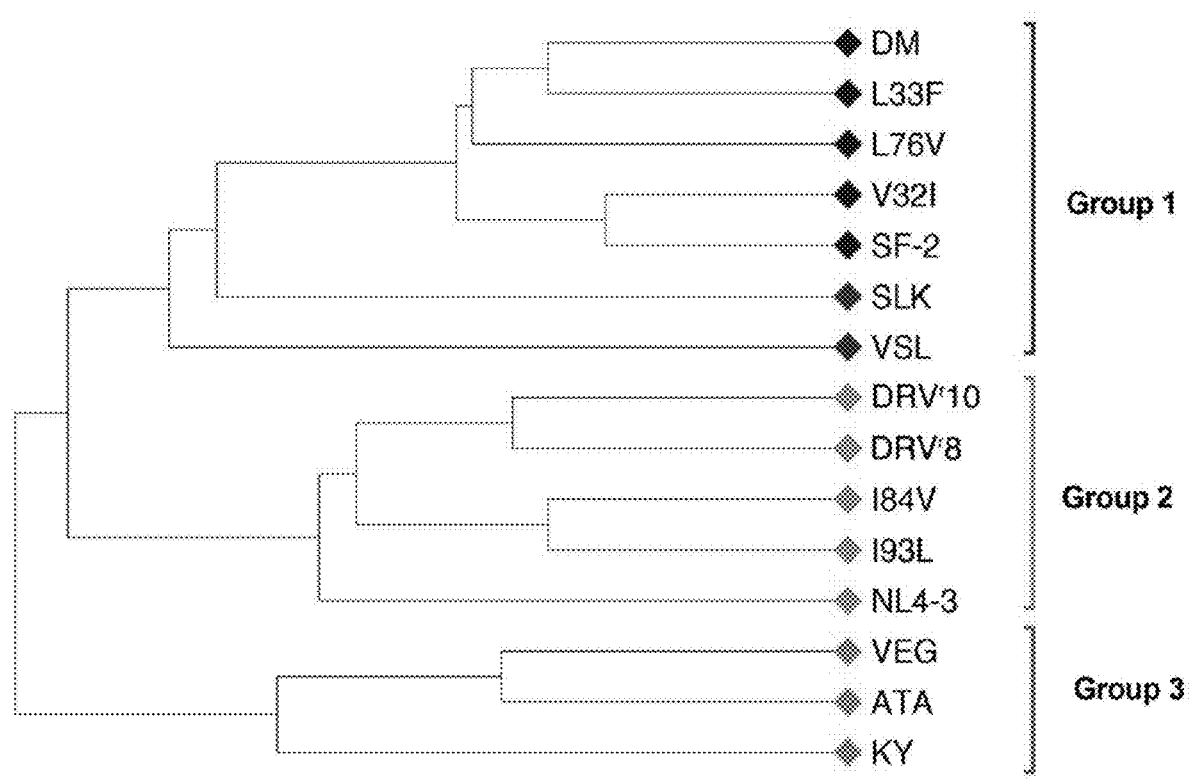
FIG. 7 is a hierarchichal clustering dendrogram of per-residue RMSF values for all 15 variants. The colored annotations are similar to FIG. 4, denoting similarity in per-residue RMSF among variants.
Figure 8:
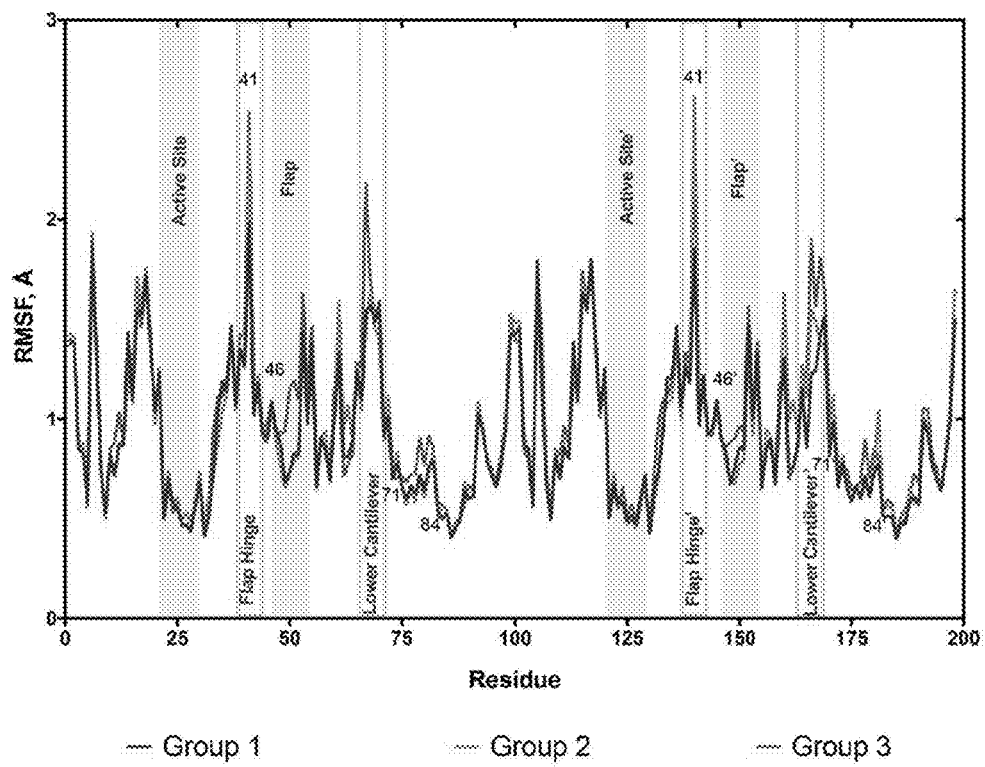
FIG. 8 is a plot of averages of variants as grouped in FIG. 6. Group colors are the same as noted in FIGS. 6 and 7.
Figures 9A, 9B, 9C:
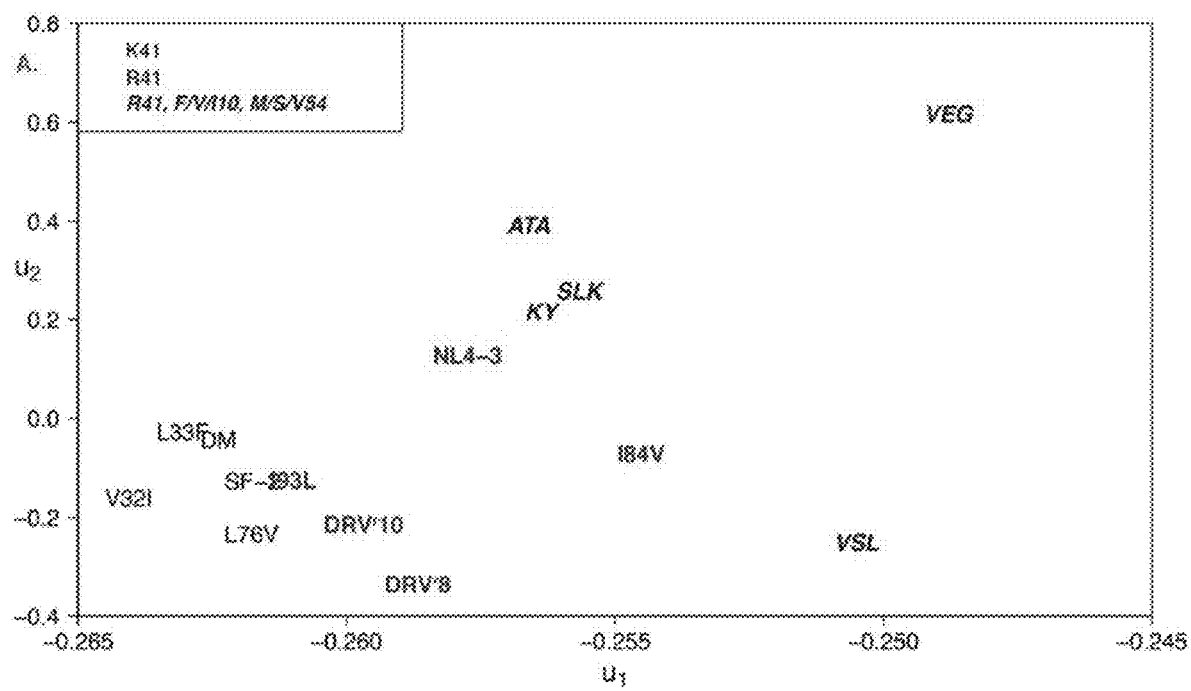
FIG. 9A is a plot of mean hydrogen bond occupancies that shared similarities with sequence and dynamics, wherein the fifteen sequence variants projected onto the first two principal components for the correlation matrix of 143 dynamic hydrogen bond occupancies. Variants were partitioned into three groups, those variants possessing K41 (black), those possessing R41, (bold, purple) and those possessing a combination of substitutions at positions 41, 10, and 54 simultaneously (bold, blue).
FIG. 9B is a list of top five single positions of FIG. 9A found to most likely underlie alterations in hydrogen bond occupancy patterns.
FIG. 9C is a list of top five position pairs of FIG. 9A found to most likely underlie hydrogen bond occupancy changes.
Figure 10:
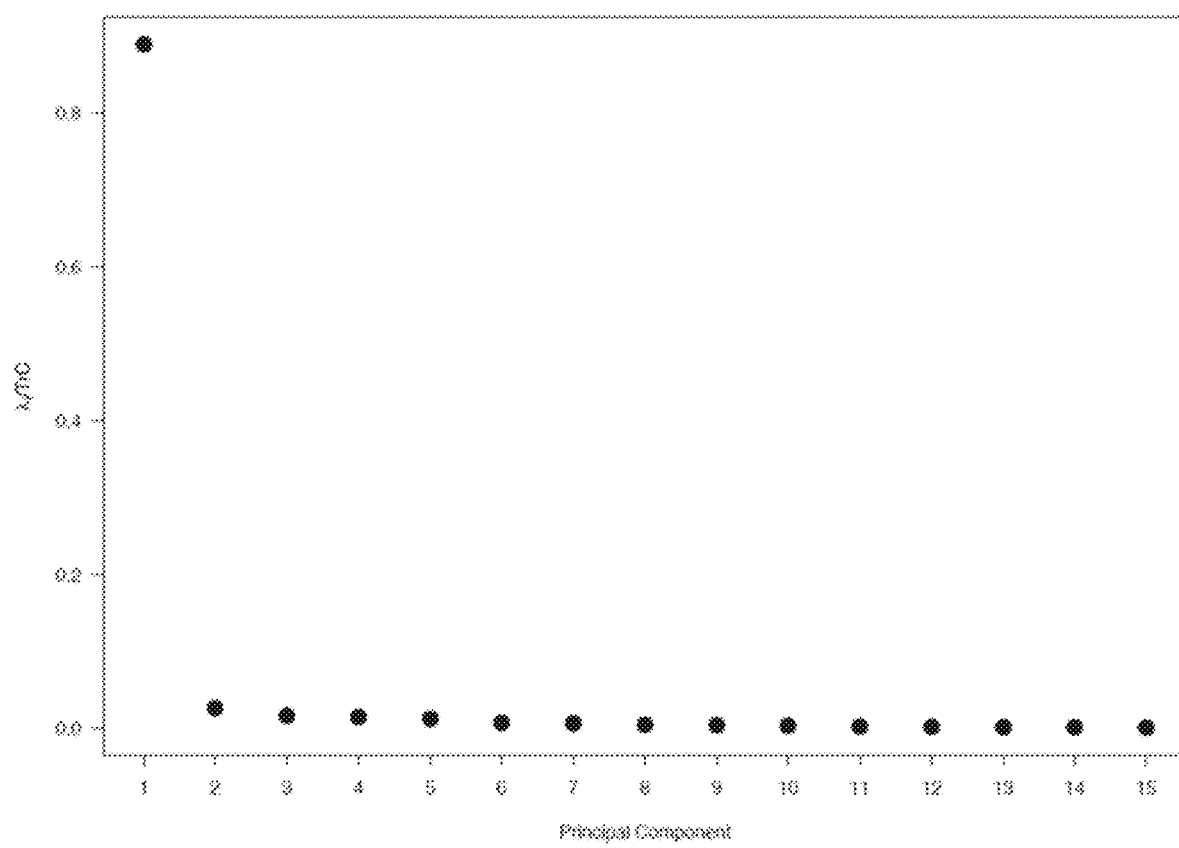
FIG. 10 is a plot of the variance of hydrogen bond occupancies among the variants that was largely accounted for by the first principal component (eigenvalue spectrum, proportion of variance), wherein the first principal component for the mean hydrogen bond occupancy dataset accounted for 89% of the variance.
Figures 11A, 11B:
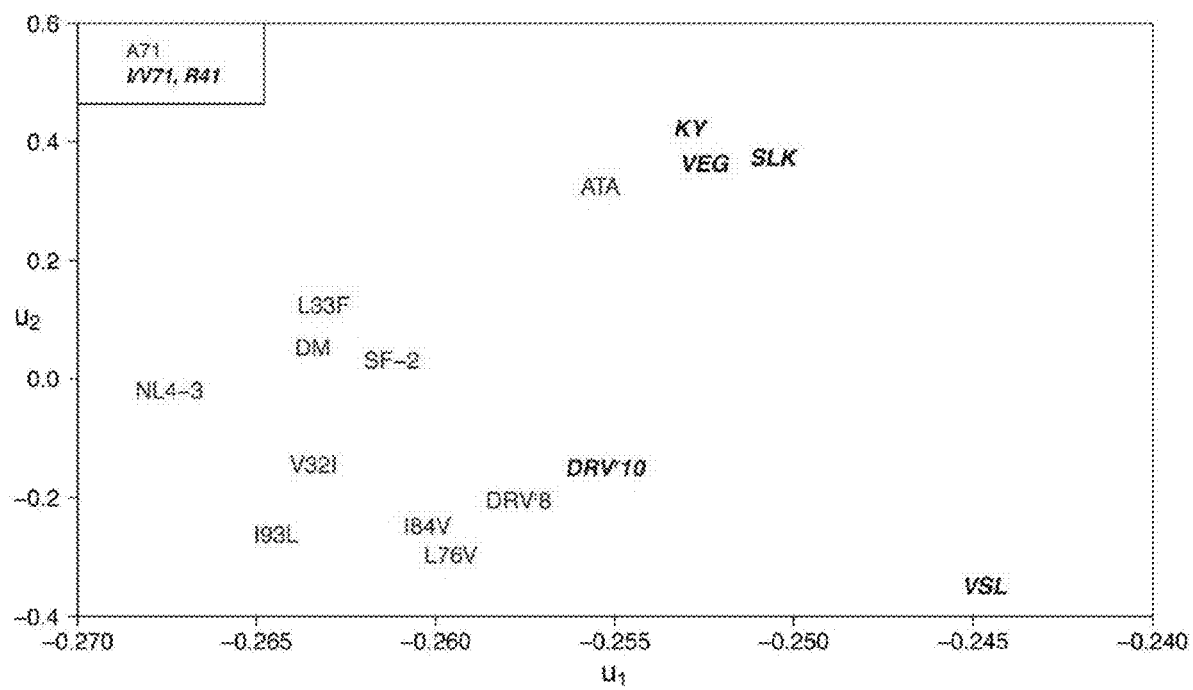
FIG. 11A is a plot of variations in mean hydrogen bond occupancies that delineated susceptibility of variants, wherein fifteen sequence variants projected onto the first two principal components for the correlation matrix of 111 dynamic hydrogen bond occupancies. Variants were partitioned into two groups, those variants bearing a substitution at position 71 (bold, blue) and those that do not (purple). Variants that contained a substitution at 71 also contained a substitution at position 41.
FIG. 11B is a list of top five single positions of FIG. 11A found to most likely underlie alterations in hydrogen bond occupancy patterns.
Figures 11C, 12:
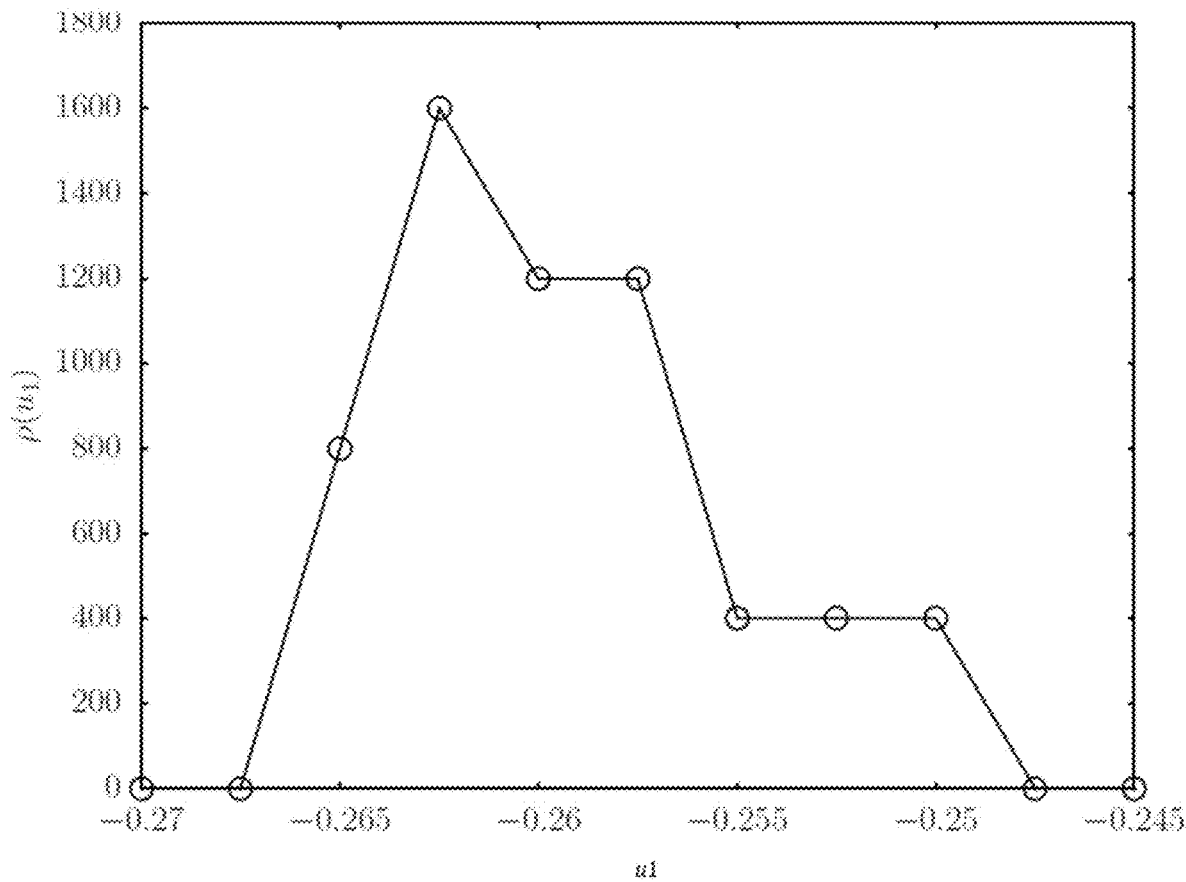
FIG. 11C is a list of top five position pairs of FIG. 11A found to most likely underlie hydrogen bond occupancy changes.
FIG. 12 is a plot of density distribution of the 15 variants along the first principal component $\rho(u_i)$ for the 111 mean hydrogen bond occupancies seen in FIG. 11A.
Figure 13:
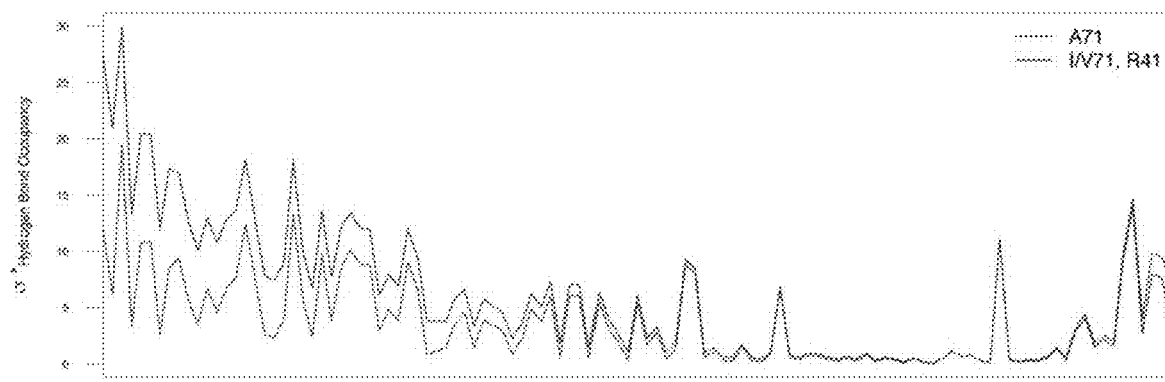
FIG. 13 are plots of dominant alterations in hydrogen bond occupancies emanating from the lower cantilever region of the protease wherein departure from the mean ($\sigma^*$) was calculated for the two groups in FIG. 11A, and wherein maximal separation between those variants lacked substitutions at position 71 (purple) and those containing substitutions at 71 (blue) occurred predominantly at hydrogen bonds formed with residues of FIGS. 13 and 14 within the 70s β-strand.
Figure 14:
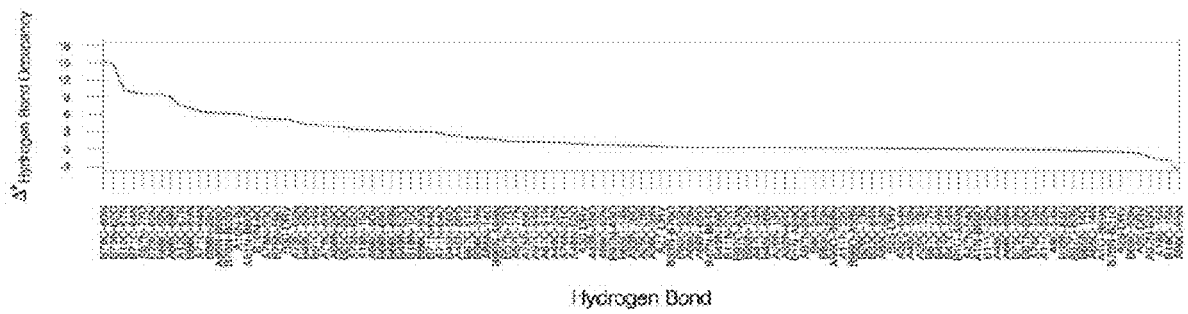
FIG. 14 is a plot of the difference between the two lines in FIG. 13 ($\Delta^*$).
Figure 15:
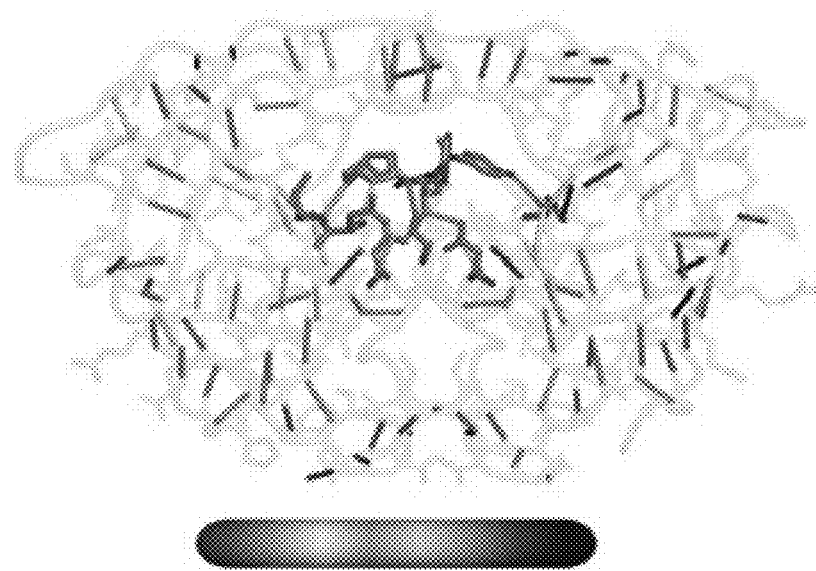
FIG. 15 is a representation of the protein wherein values were plotted onto the structure from red (high variability) to blue (low variability).
Figure 16:
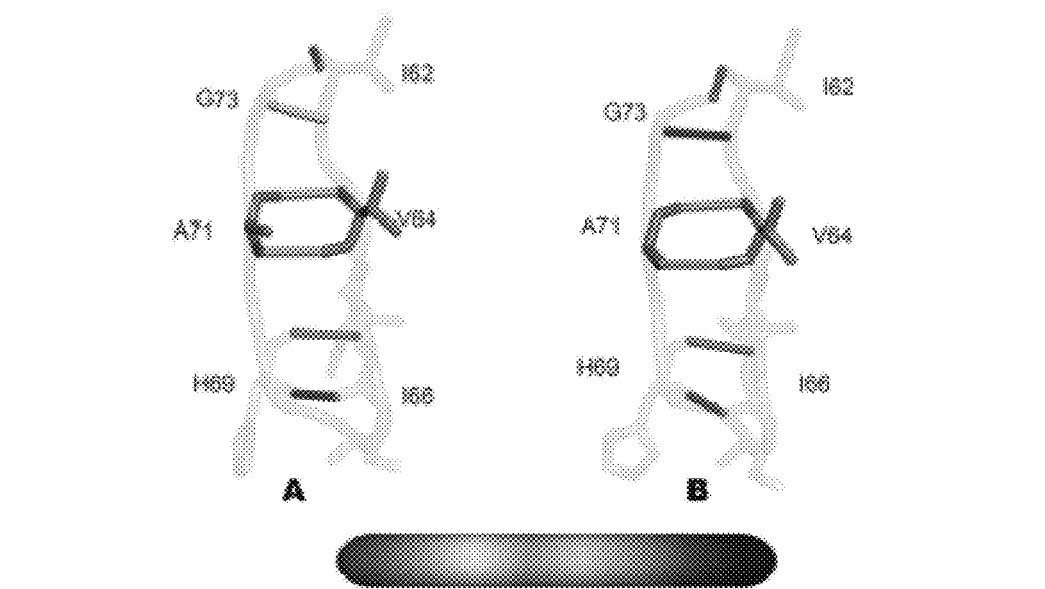
FIG. 16 is a representation of hydrogen bonds formed between residues surrounding the substitution at 71 as labeled, for both monomers of the protease. Hydrogen bonds in this region had higher alterations in chain B than in chain A.
Figure 17:
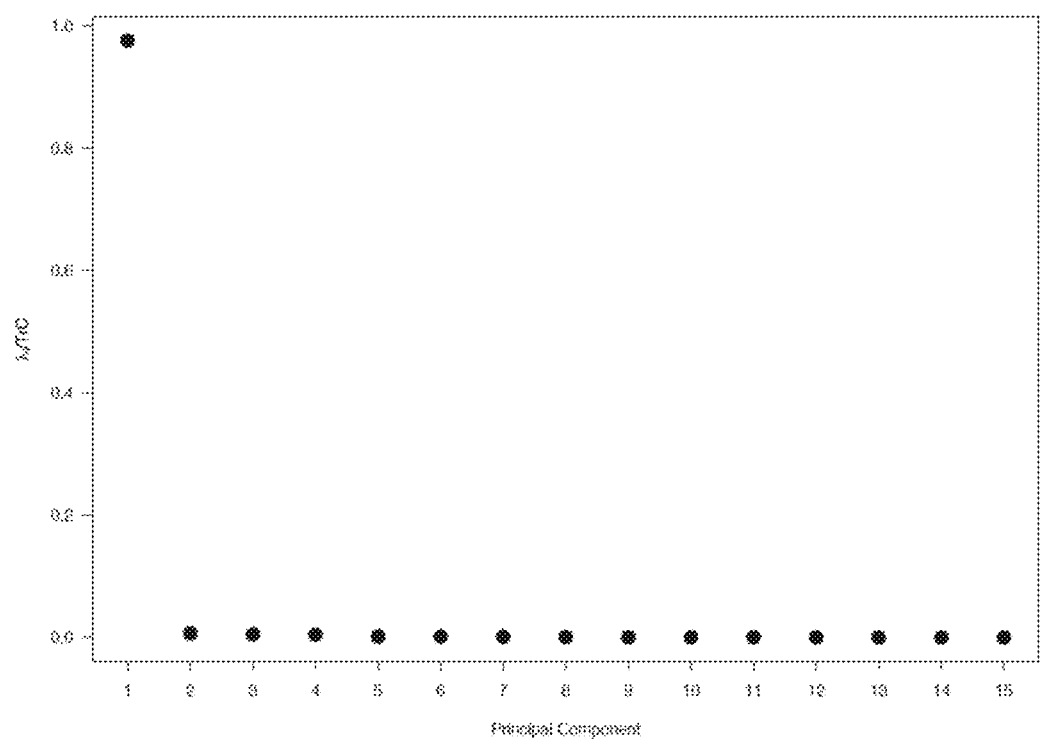
FIG. 17 is a plot of the variance of mean van der Waals energy accounted for by the first principal component (eigenvalue spectrum, proportion of variance), wherein the first principal component for the mean van der Waals energy dataset accounted for 97.6% of the variance.
Figures 18A, 18B, 18C:
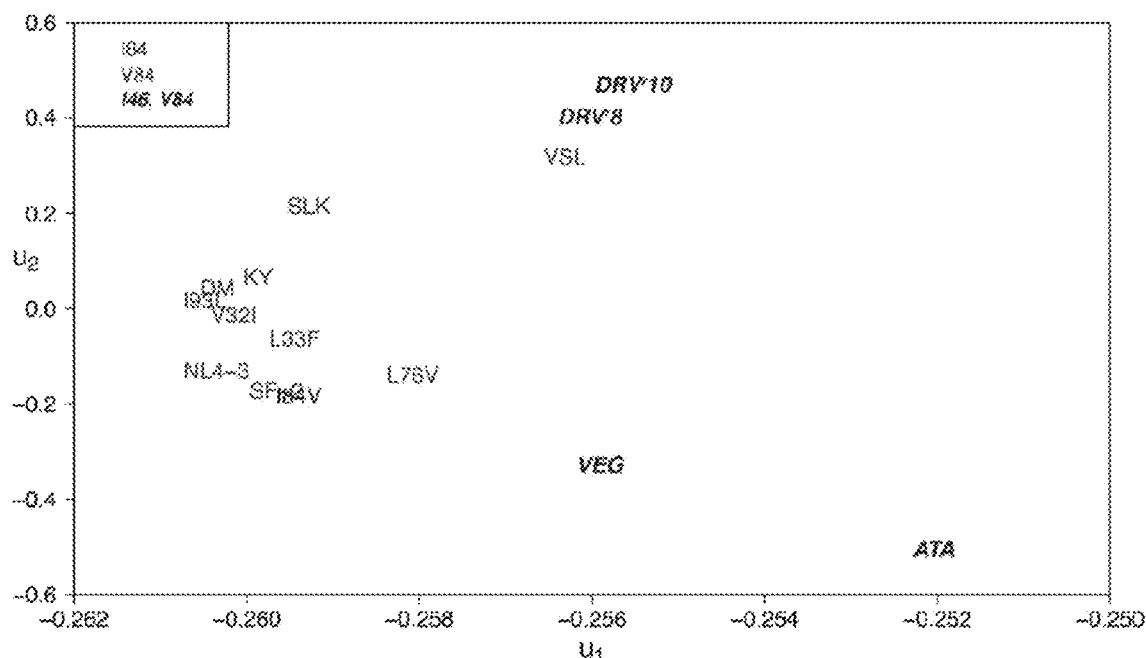
FIG. 18A is a distribution of ligand-protease van der Waals contact energies that revealed energetic similarities between single site accessory RAMs and clinically derived variants, wherein fifteen sequence variants were projected onto the first two principal components for the correlation matrix of 64 mean protease-DRV van der Waals contacts, and wherein variants were partitioned into two groups, those that bore substitutions at positions 84 and/or 46 (blue) and those that did not (purple), similar to FIG. 11A.
FIG. 18B lists top single positions of FIG. 18A that most likely underlay changes in van der Waals contact energies.
FIG. 18C lists top paired positions of FIG. 18A that most likely underlay changes in van der Waals contact energies.
Figure 19:
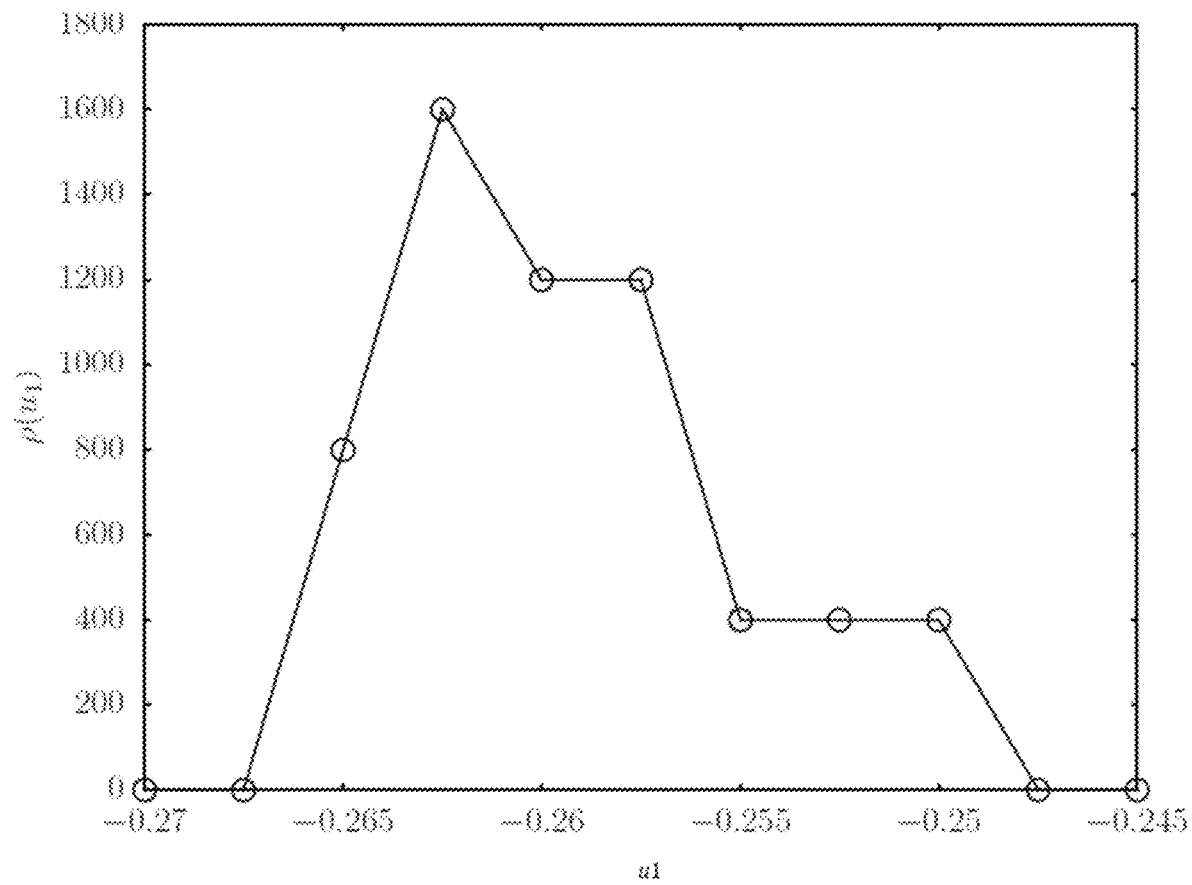
FIG. 19 is a plot of density distribution of the 15 variants along the first principal component $\rho(u_1)$ for the 64 mean van der Waals contact energies seen in FIG. 18A.

At least one second script was applied to the set of tensors to integrate the set of tensors with the experimental binding data corresponding with each member of the protein-ligand complex family to form a primary image of the binding site. For these two data sets, a combination of Eigenvalue decomposition, which is one method by which tensors are evaluated, and statistical testing was used to identify mutations that best explained the observed variance in physical properties across the protease panel FIGS. 9-23.

Alterations in hydrogen bonding network were analyzed to thereby distinguish single and double mutants from the more complex variants. A71V and R41K, a known resistance-associated mutation and a polymorphic substitution respectively, also impacted the hydrogen-bonding network FIGS. 9-17. In addition, the primary mutation I84V in conjunction with the peripheral accessory mutation M46I and several other remote accessory mutations gave rise to alterations of van der Waals contacts with DRV FIGS. 18-23. Thus, combining MD simulations of a diverse set of HIV-1 protease variants, both susceptible and resistant to inhibition, with unsupervised machine learning techniques yielded mechanistic insights into how distal accessory mutations contributed to drug resistance.

II. Results

To determine which variable positions specifically impact the structural and dynamic properties of protease-DRV binding, a combination of inhibitor-bound crystal structures and homology models were used as input for MD simulations for 15 variants of HIV-1 protease. Details of the models, nomenclature for the variants, and MD simulations are described below in the Methods section. Using the resulting trajectories, root mean square fluctuations (RMSF), mean per-residue contact energies with DRV, and hydrogen bond occupancies throughout the protease were monitored for the panel of protease variants.

Convergent Evolution Drove Protease Resistance in Independent Viral Lineages

A diverse panel of 15 HIV-1 protease variants was chosen with a broad range of sequence substitutions containing single site mutants and more heavily mutated multi-drug resistant proteases (MDR-PRs). Both the SF-2 and NL4-3 wild-type (WT) proteases were used as controls for the variants in the panel. These two WT proteins shared 95% identity, varying at positions 7, 14, 41, 63 and 64 (FIG. 2). Both SF-2 and NL4-3 have high susceptibilities to DRV, with single-digit pM $K_I$ values[16] at the limit of detection by enzymatic assays and an $EC_{50}$ of 4 nM in cell-based replicon assays. Table 1 is a listing of $EC_{50}$ values for clinically-derived HIV-1 protease variants determined by cell-based assays at the Swanstrom laboratory at UNC-Chapel Hill, and fold changes relative to wild type NL4-3. The $EC_{50}$ value for variant $ATA_{21}$ could not be determined.

TABLE 1

$EC_{50}$ Values for Clinically-Derived Variants

| | $EC_{50}$ In nM | Fold Change $EC_{50}$ |
|---|---|---|
| NL4-3 | 3.98 | |
| $ATA_{21}$ | — | — |
| $KY_{26}$ | 1160 | 291 |
| $SLK_{19}$ | 32.5 | 8 |
| $VEG_{23}$ | 7800 | 1960 |
| $VSL_{23}$ | 320 | 80 |

Of the highly mutated proteases in the panel, two were obtained from long-term viral passaging experiments ($DRV^r8$ and $DRV^r10$), conducted under DRV selective pressure. These two protease sequences differed from the NL4-3 WT by 8 and 10 amino acid substitutions, respectively (FIG. 2). The remaining MDR proteases were obtained from the HIV Drug Resistance Database.[18-19] The patient-derived MDR-PRs contained between 19 and 26 substitutions when compared to the SF-2 WT protease[7]. Taken together, the panel of 15 proteases had sequence variations at 50 of the 99 amino acid positions within each monomer (FIGS. 2 and 3).

Although the viral population ancestry and temporal treatment history was not annotated for the patient-derived proteases in the simulation panel, they share common mutations with one another and also with the highly mutated variants derived from viral passaging experiments (FIGS. 2A and 2B). Based on the dates when the samples were isolated and the high level of resistance to DRV inhibition (Table 1), there was a possibility that one patient-derived strain, $VEG^{23}$, was exposed to DRV treatment.

Considering the resistance to DRV inhibition in the $DRV^r8$ and $DRV^r10$ strains that was evident from viral passaging experiments, the measured resistance among the patient-derived strains (Table 1) and the shared sequence identities within the panel, cross-resistance to DRV among the patient isolates was apparent. These observations suggested that the phenotypes of these proteases converged under the selective pressure of inhibition, perhaps driving similar mechanisms of resistance. A phylogenetic tree based on their sequences for the 15 proteases in the panel is shown in FIG. 4.[20]

Sequences of Multi-Drug Resistant Mutants Correlated with Changes in Protease Dynamics The protease variants with available DRV bound structures were SF-2 (PDB: 1T3R), L76V, V32I and V32I/L33F.[17,21] The NL4-3 wild type and remaining variants were modeled based on the DRV-bound wild-type SF-2 structure. The crystallographic water molecules, including the important bridge water between the inhibitor and the protease flaps, were preserved in each model. Three 100 ns replicate MD simulations with explicit solvent were performed and analyzed for each DRV complex.

The root mean square deviations (RMSD) revealed that the accumulation of mutations from single site to patient-derived variants led to greater structural changes in order to reach thermal equilibrium starting from the modeled configuration (FIGS. 5A-5C). The changes in per-residue root mean square fluctuations (RMSF) about the mean appeared to correlate well with protease lineage with the most pronounced changes in fluctuation seen in the flaps, flap hinge, and lower cantilever regions of the protease while the catalytic aspartate residues remained rigid relatively across the simulations (FIG. 6). Hierarchical clustering of the per-residue RMSF profiles for the fifteen variants resulted in similar groupings to those within the sequence-based phylogenetic tree (FIGS. 4 and 7). This overlap of clustering suggests that sequenced similarity alone appeared to be a good predictor of similar backbone dynamics because the regions of high variability contained residues found to be predictive of changes in dynamics (FIG. 8).

Figure 20:
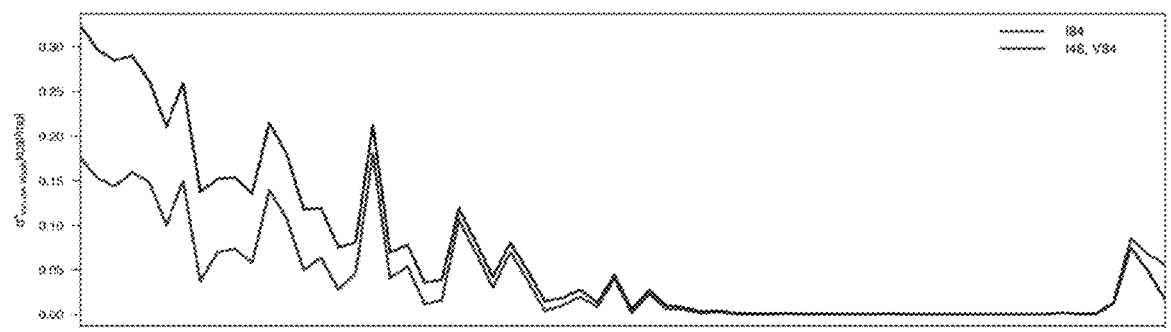
FIG. 20 is a plot of a mutations caused perturbations of some non-mutable active site residue van der Waals contacts wherein departure from the mean ($\sigma^*$) was calculated for two groups in known protease inhibitor of NS3/4A protease associated with hepatitis C virus (HCV), and Influenza Neuraminidase inhibitors, such as Tamiflu.
Figure 21:
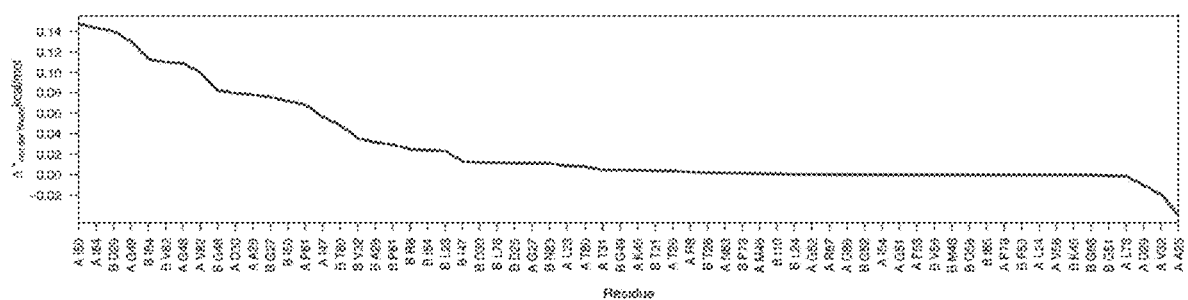
Figure 22:
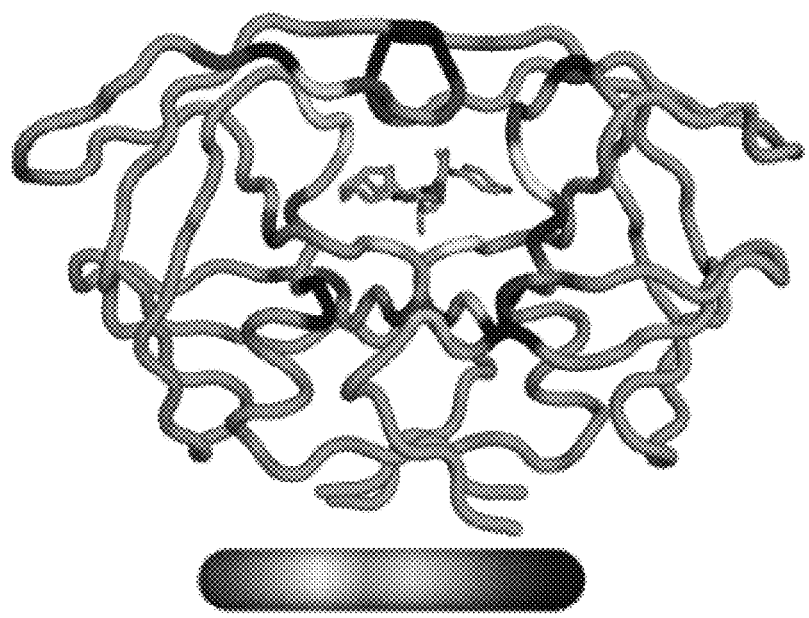
Figure 23:
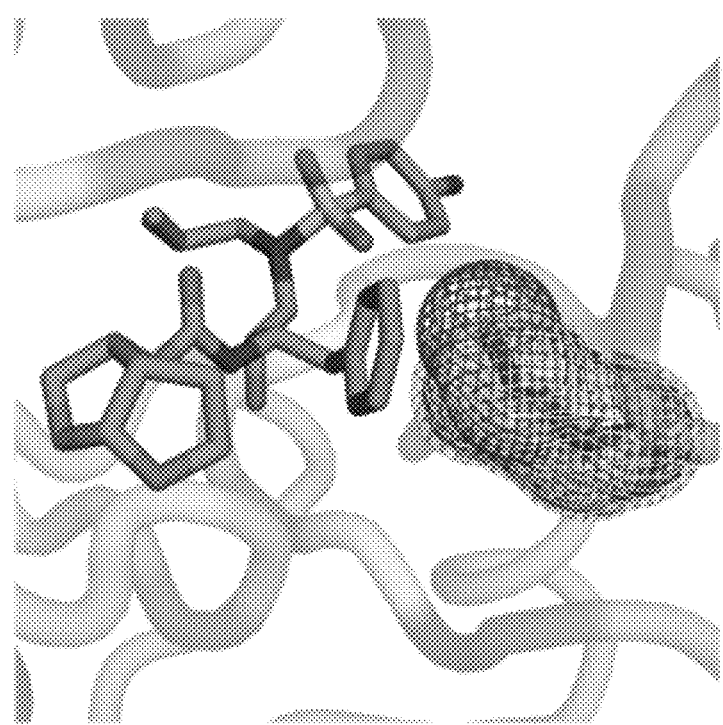

Alterations in Hydrogen Bonding Correlated with Particular Combinations of Mutations To characterize alterations in the hydrogen bonding observed among the variants and to determine which variable positions best explained alterations in hydrogen bond network among the proteases, a set of 143 hydrogen bonds (111 main chain and 32 side chain) were monitored over the simulations. This set included both intra-protease and protease-DRV hydrogen bonds. With an expanded panel of protease variants, relative to an earlier study,[17] the use of algorithms for detecting patterns of altered occupancies and identifying specific mutations that may underlie these alterations became essential. A combination of principal component analysis (PCA), to detect alterations, followed by hypothesis testing based on amino acid substitution at specific sites in the protease, was employed. To begin, a 15×15 correlation matrix of mean occupancies for these 143 main and side chain hydrogen bonds was computed and used for PCA (see Methods, infra, for details). The first principal component (FIG. 9A-9C), $u_1$, accounted for nearly all (89%, see FIG. 10) of the inter-variant variance in hydrogen bond occupancies. Comparing the ordering of protease variants along $u_1$, a striking similarity was observed with the phylogenetic ordering (FIG. 4), suggesting that variations in overall hydrogen bond occupancies were dictated by lineage.

Focusing on the 111 main chain hydrogen bonds plus the 2 catalytic aspartate-DRV side chain bonds (excluding the other side-chain hydrogen bonds), the resistant variants tended to have higher values of the first principal component (FIGS. 11A-11C) than the more susceptible variants, including the two wild-type strains. To infer which amino acid substitutions at specific positions in the protease accounted for the distribution of variants along $u_1$, it was noted that the density, $\rho(u_1)$, of variants along this component was approximately bimodal (see FIG. 12), hypothesis tests were performed using the Wilcoxon rank sum.[22] The hypothesis tests were conducted for pairs of distributions defined by the presence or absence of a specific mutation (e.g. I84V). The null hypothesis showed no difference between the means of these two distributions. There was a lower bound on the p-value, defined by $\rho(u_1)$. FIGS. 11A and 11B summarize the results of these tests, identifying A71V as the single mutation that best accounts for the spread in hydrogen bonding patterns among the variants in the panel. Segregating the variants based on this mutation, we found that DRV$^{r}$10, KY,[26] SLK,[20] VEG[24] and VSL[24] all contained changes at position 71 (FIG. 11A). To determine whether pair-wise substitutions of amino acids could be used to better recapitulate the bimodal distribution of variants with respect to $u_1$, additional statistical tests were performed: no pair or other combination of substitutions explained more of this variance than did the A71V/I mutation alone (FIG. 11C).

The variance in hydrogen bonding within this panel could be further explained by classifying the variants into those that contained mutations at 10, 54, 71 and 41 simultaneously, and those that did not. Only the patient variants mentioned above contained this combination of mutations. While protease mutations at residue 41 were considered polymorphic, such mutations have been reported to play a role in resistance to protease inhibitors, including DRV.[23] Nonetheless, residue 41 was one of five residues whose changes distinguished the variants in the panel in an NL4-3 background from those in the SF-2 background. This finding suggested that mutations at positions 10, 54, 71 and 41, being distal to the active site, may have been relaying information about the global dynamics of the protein, consistent a hypothesis that mutations perturbed the dynamic ensemble of the protease via the network of hydrogen bonds.[16, 23] The majority of variants in the panel contained very pronounced changes throughout the lower cantilever region of the protease, which included residue 71 (FIGS. 13-16).

Distal Accessory Mutations Altered Ligand-Protease Van Der Waals Interactions

Using the approach described above, amino acid substitutions that played key roles in altering the hydrophobic contacts of the protease with DRV were determined. The mean van der Waals (vdW) contact energies between the protease active site residues and DRV were calculated over the trajectories for each of the variants in the panel. Energies were collected for all 64 amino acids within the protease active site that had contacts with DRV during the simulations. Inspecting the distribution of the variants along the first principal component of the resulting correlation matrix, which accounted for 97.6% of the inter-variant variance of van der Waals (vdW) energies (FIG. 17), the variants segregated differently than when the internal hydrogen bonding was analyzed. The variants KY[26] and SLK[19] segregated with both WT proteases and some single site variants as well (FIGS. 18A-18C).

Following the same hypothesis testing approach, as explained above for mean hydrogen bond occupancies, I84V was determined to be the most predictive single site substitution for classifying the variants (FIG. 18B). Segregating the variants based solely on the presence of I84V captured most of the observed bimodality in $\rho(u_1)$ (FIG. 19), such that variants ATA[21], VEG[23], KY[26], DRV$^{r}$8, DRV$^{r}$10 and, necessarily the I84V single mutant, were distinguished from the remainder of the protease panel (FIG. 18A). The change from isoleucine to valine reduces the close packing of the isoleucine side chain and the P1' phenylalanine-mimicking moiety of DRV (FIG. 23).

Among the candidate pairs of mutational sites, the pair of residues that is most predictive of the perturbations of the vdW contact energies was I84V and M46I (FIG. 18C). Segregating the variants based on this combination of mutations, $ATA_{21}$, VEG[23], DRV$^{r}$8 and DRV$^{r}$10 can be distinguished from the rest of the panel (FIG. 18A). Furthermore, combination of substitutions at positions 13, 32, and 33 in addition to I84V were predictive of the distinguishing patterns within the vdW data. All four of the variants which contained an amino acid substitution at positions 84 and 46 also contained mutations I13V, V32I and L33F. This finding suggested that there may have been some coupling between mutations at positions 84, 46, 13, 32 and 33 which resulted in the weakening of protease-DRV binding.

With the exception of primary resistance mutation I84V, these mutations were accessory mutations not located directly at the active site, which caused alterations in vdW contacts of other active site residues. In addition to I84, among the 64 active site residues that made vdW contacts with DRV, D30 and 150 in chain A and R8, D29, D30, G27, G48, and V82 in chain B, were perturbed the most by accessory mutations, as indicated by the departure from the mean for all residues across the 15 proteases (FIG. 20; see also Methods, infra). These distinguishing variations in vdW contacts mostly impact generally immutable active site residues, which suggested that preserving mostly hydrophobic contacts upon inhibitor binding was crucial for sustained targeting (FIG. 21). Mapping the difference (Δ*, FIG. 20) in departure from the mean values (σ*) onto the structure further details how vdW contacts of active site residues were impacted by distal mutations (FIG. 22).

III. Discussion

The accumulation of mutations within a drug target allowed the balance of substrate processing versus inhibitor binding to tip in favor of the former. The HIV-1 protease exhibited a high level of resiliency under selective pressure and resistant HIV-1 protease variants were sufficiently adapted to evade inhibition without a substantial growth penalty.[25] The constellation of resistance-associated mutations that arose throughout the rest of the protein, as was the case with DRV, has been relegated to aiding in recovery of viral fitness.[26-28] Here, the role of non-active site mutations in conferring drug resistance, by analyzing 15 protease variants that together contain substitutions at 50 of the 99 amino acid positions within the enzyme was examined. Specifically, the effects of mutations on protease structure and dynamics were characterized by hydrogen bonding, and vdW contacts with the inhibitor. Specific positions were identified that accounted for the variance in these properties, including mutations at residues away from the active site.

Mutations compromise the hydrogen bonding and vdW contacts necessary for DRV binding to ensure that the mutations render the protein resistant while retaining its biological function.[17] Here, a novel combination of MD simulations and unsupervised machine learning was employed to characterize the variability in these functionally important quantities across a panel of 15 susceptible and resistant protease variants and identify specific mutations that explained this variability. The specific mutations that were identified validated the significance of previously observed mutations occurring outside the active site. For example, variants that had mutations at residue 71 were observed to be a major contributor to the variance of the hydrogen bonds. The A71V mutation has been shown previously to be a key mutation in the re-stabilization of the enzyme in the presence of major mutations such as I50L/V, and has also been shown to propagate its effects from its resident position in the lower cantilever region of the protease to the active site via the hydrogen bond network of the protein.[26-27 29-33] Overall, we identified mutations that were highly predictive of changes in the hydrogen bonding that were all distal to the active site and mostly involved changes to larger hydrophobic residues. This result suggested a 'domino' effect model, consistent with previous findings[17,27,33-34] that was driven by mutations in residues distal from active site whose impact propagated to the active site of the protein.

The presence of I84V mutation was the best predictor of alterations in vdW contacts with the inhibitor, in combination with M46I. The I84V mutation was common in protease inhibitor cross-resistance. The change from the bulkier beta-branched isoleucine to the smaller valine has been the Achilles heel of PI treatment since the I84V mutation was first observed in saquinavir treatment.[35] M46I was thought to only be a compensatory mutation[25] until early MD studies found it to be a key modulator of flap dynamics.[36] The combination of I84V with M46I has been long studied as a major/minor co-mutant pair in the midst of other compensatory mutations able to drive resistance to early PIs.[25,37] With the exceptions of V32I, which is at the periphery, the remaining mutations that were identified here as to underlie the observed variance in the vdW contacts were outside of the active site and were previously explored for their compensatory effects.[7] FIGS. 20-23 illustrate that the residues with the highest variability in vdW contact energies were within the active site (G48, I50, I84, G27' and I84'), while the specific mutations that regulate this variability were either juxtaposed or distal to the active site.

The analysis presented herein demonstrated how mutations outside of the active site impacted DRV targeting. Mutations distal to the active site, whether they occurred as single amino acid substitutions or as highly complex combinations, were able to perturb inhibitor binding through changes in certain key interactions between the enzyme and inhibitor. Overall backbone dynamics could be associated with sequence similarity, and could change with accumulating mutations and drug resistance. While primary mutations were known to drive resistance in HIV-1 protease, these findings delineated the significant contributions of accessory mutations to resistance.

IV. Methods

Protease Panel and Nomenclature

The panel of 15 proteases used in this study consisted of the SF-2 and NL4-3 wild-type proteases along with 13 mutant variants. The WT proteases served as controls for the variants with respect to their subtype B backgrounds and laboratory origin. The L76V, V32I and V32I/L33F (PDB accession codes 3OY4, 4Q1X and 4Q1Y respectively) variants were taken from a previous study.[17] To this group of single and double mutants, the L33F single mutant was added. Another set of protease sequences were obtained from HIV-1 cell culture passaging studies in the presence of DRV. Briefly, in vitro selections were carried out with DRV using an initial mixture of 26 variants, each containing a single resistance mutation. The selections were carried out with increasing inhibitor concentrations between with final drug concentrations that were 1000-fold greater than the measured $IC^{50}$ in WT strains. Using the Primer ID-based paired-end MiSeq platform,[38] mutations in the protease were analyzed based on RNA sequencing carried out at four time points (i.e. passage checkpoints) as inhibitor concentration was increased. The variants in this set include homology models of single site I93L and I84V variants complexed with DRV along with a variant containing eight mutations ($DRV^r8$) and a variant containing 10 mutations ($DRV^r10$) in an NL4-3 background. The two highly mutated variants, $DRV^r8$ and $DRV^r10$, were present at very high concentrations of DRV.

The remaining variants in the panel were selected from the patient-derived proteases in the HIV Drug Resistance Database.[18-19] This group of proteins contained 19-26 mutations compared to the SF-2 WT protease.[7] Each patient variant was named based on which amino acid substitutions were unique to that variant and the number of mutations it contained compared to the SF-2 WT. For example, variant $KY_{26}$ was the only variant that contained substitutions H69K and C67Y and it had 26 mutations. All other variants were named for the mutations they contained (e.g. variant I84V only contained this mutation). The V32I+L33F double mutant was referred to as DM for "double mutant."

Homology Modeling and MD Simulations

The SF-2 WT, L76V, V32I and V32I/L33F protease sequence variants had available crystal structures bound to DRV. The NL4-3 wild-type and remaining variants were all modeled based on the DRV bound structure (PDB ID: 1T3R). The crystallographic water molecules, including the important bridge water between the inhibitor and the protease flaps, were preserved in each model, as was DRV. Using the Prime Structure Prediction Wizard by Schrödinger (Release 2014-4, Schrödinger LLC, New York, N.Y.[39-40]), each of the 11 variant sequences was used as a query to search for homologs via BLAST.[41] Both chains of PDB structure 1T3R were selected as templates to build the homodimer containing the appropriate variant sequence. Once the model was prepared, the structure was built retaining the ligand from the template structure. Water molecules from the template structure were added to the newly built variant structure and the side-chains of those residues that were mutated in silico were refined locally using Prime Refinement Tools followed by a complete refinement of the overall structure in the Protein Preparation Wizard. This utility processed the structures by assigning bond orders, adding hydrogen atoms, creating disulfide bonds, and filling in missing sidechains using Prime. Next, tautomerization states were optimized using Epik and hydrogen bond networks and protonation states were determined and optimized using PROPKA pH 7.0, with exhaustive sampling of water orientations and minimization of the hydrogen atom configurations of altered species. Finally, interaction energies of hydrogen atoms were minimized using the Impact Refinement Module and the OPLS2005 force field.

All MD simulations were performed using Desmond[42-45] with the OPLS2005 force field. Systems were prepared by solvating the structure in a cubic box that extended at least 10 Å beyond the nearest solute atom in all directions using the TIP3 water model.[46] Sodium chloride was added to the equivalent of 150 mM to simulate physiological conditions. The system was neutralized by adding counterions as needed ($Na^+$ or $Cl^-$).

The rigorous pre-equilibration model was employed as described elsewhere.[47] Briefly, a series of restrained minimization steps was performed to gradually relax the system. Initially all heavy solute atoms were restrained with a force constant of 1000 kcal $mol^{-1}$ $Å^{-2}$ for 10 steps of steepest decent followed by up to 2000 steps using the LBFG method to a convergence of 50 kcal $mol^{-1}$ $Å^{-2}$. Restraints were removed from side-chains using LBFG for 5000 step or until a convergence of 50 kcal $mol^{-1}$ $Å^{-2}$. The restraints on the backbone were gradually removed using the following decreasing force constants: 1000, 500, 250, 100, 50, 10, 1 and 0 50 kcal $mol^{-1}$ $Å^{-2}$ using the LBFG method to convergence of 50 kcal $mol^{-1}$ $Å^{-2}$.

A series of short pre-production MD simulations were performed to equilibrate the system, starting with a 10 ps simulation in the NVT ensemble with 50 kcal $mol^{-1}$ $Å^{-2}$ harmonic restraints on solute heavy atoms using the Berendsen thermostat[48] at 10 K. A 1 fs time-step was used for bonded and short-range interactions (up to 9 Å) and a 3 fs time-step was used for long-range electrostatic interactions. A 10 ps MD simulation followed, using an NPT ensemble with a Berendsen thermostat followed, run at 10 K with a 2 ps time-step for bonded and short-range interactions and 6 fs for long-range electrostatics. Over 50 ps, the temperature of the system was increased to 300 K with restraints on heavy solute atoms followed by a 10 ps simulation where all harmonic restraints were removed. Production simulations were performed in the constant NPT ensemble using the Desmond implementation of the Martyna-Tobias-Klein (MTK) extended system.[49] Simulations were carried out with no harmonic restraints for 100 ns at 300 K and 1 bar. The cut off for non-bonded interactions was 9 Å; the smooth particle mesh Ewald (PME) method[50] was applied; the time-step was 2 fs for short-range interactions and 6 fs for long range interactions. All simulations were performed in triplicate, each with different random initial velocities for a total production time of 300 ns for each of the 15 simulated protease systems. The Simulation Event Analysis Tool within Maestro was used to determine the mean occupancies of 143 inter and intra-main chain and side chain hydrogen bonds, along with hydrogen bonds between the ligand and protease. In order to facilitate analysis, including computation of the mean protein-ligand van der Waals interaction energies, Visual Molecular Dynamics (VMD) version 1.9.2[51] was used to translate the Desmond trajectories to PDB format.

Evaluation of Hydrogen Bonding and Van Der Waals Interactions

For each hydrogen bond pair, the donor heavy atom along with its hydrogen and the acceptor atom were specified for calculation of hydrogen bonding occupancy. For each frame, only pairs that satisfied the hydrogen bond geometric criteria as set forth by Schrödinger were chosen: the distance between hydrogen atom and acceptor atom had to be less than or equal to 2.5 Å, the angle between donor heavy atom and its hydrogen and the acceptor had to be at least 120°, and the angle between the hydrogen and acceptor heavy atom had to be at least 90°. The van der Waals contacts between the inhibitor and the protease were calculated using a simplified Lennard-Jones potential, following published protocols.[52]

Principal Components Analysis and Statistical Testing

The hydrogen bond and van der Waals observations were combined into matrices of dimension 15×N, where N was the number of observations in each data set (for example, there were N=64 protein-ligand van der Waals energies per variant). The correlation matrix was employed in lieu of a covariance matrix so that any outlier data would not dominate the variance in the data set. Principal components were defined in terms of an eigenvalue problem for the correlation matrix: $cu_i = \lambda_i u_i$ where C was the correlation matrix for any two variables X and Y;

$$C = \frac{\langle (X - \langle X \rangle)(Y - \langle Y \rangle) \rangle}{\langle (X - \langle X \rangle) \rangle \langle (Y - \langle Y \rangle) \rangle}$$

This problem was solved by diagonalization $C = UC'U^{-1}$ where the diagonal elements of C' are ordered components of the variance (i.e. the eigenvalues $\lambda_i$). This transformation preserved the trace of matrix C (TrC=TrC'). The proportion of total variance, TrC, that was explained by eigenvector $u_i$ was defined as $$\frac{\lambda_i}{TrC}.$$

Eigenvalues and eigenvectors were calculated using an R interface to the LAPACK (Linear Algebra Package) library.[53] With the van der Waals and hydrogen bonding data, the explained variance was dominated by the first eigenvector (or principal component) and hypothesis testing was used to interpret the spread among the different protease variants. For each mean hydrogen bond occupancy or van der Waals contact, the following quantity was computed in order to measure how the within-class observations deviated from the global average for each of two classes of variants (e.g. those with or without the I84V mutation):

$$\sigma^* = \sum_{j=1}^{N_{class}} \sqrt{(E_j - \mu)^2}$$

where $N_{class}$ was the total number of variants in each class, $E_j$ was the van der Waals contact for variant j and μ was the average across all 15 variants. This deviation allowed identification of important, or at least highly variable residue interactions. The difference between σ* for two classes, A and B, was defined as $\Delta^* = (\sigma^*_A - \sigma^*_B)$.

REFERENCES (1) Tenore, S. B.; Ferreira, P. R. The Place of Protease Inhibitors in Antiretroviral Treatment. Braz. J. Infect. Dis. 2009, 13, 371-374.
(2) Wang, Y.; Liu, Z.; Brunzelle, J. S.; Kovari, I. A.; Dewdney, T. G.; Reiter, S. J.; Kovari, L. C. The Higher Barrier of Darunavir and Tipranavir Resistance for HIV-1 Protease. Biochem. Biophys. Res. Commun. 2011, 412, 737-742.
(3) Bethell, R.; Scherer, J.; Witvrouw, M.; Paquet, A.; Coakley, E.; Hall, D. Phenotypic Protease Inhibitor Resistance and Cross-Resistance in the Clinic from 2006 to 2008 and Mutational Prevalences in HIV from Patients with Discordant Tipranavir and Darunavir Susceptibility Phenotypes. AIDS Res. Hum. Retroviruses 2012, 28, 1019-1024.
(4) King, N. M.; Prabu-Jeyabalan, M.; Nalivaika, E. A.; Wigerinck, P.; de Bethune, M. P.; Schiffer, C. A. Structural and Thermodynamic Basis for the Binding of TMC114, a Next-Generation Human Immunodeficiency Virus Type 1 Protease Inhibitor. J. Virol. 2004, 78, 12012-12021.
(5) Ghosh, A. K.; Chapsal, B. D.; Weber, I. T.; Mitsuya, H. Design of HIV Protease Inhibitors Targeting Protein Backbone: An Effective Strategy for Combating Drug Resistance. Acc. Chem. Res. 2008, 41, 78-86.
(6) Nalam, M. N.; Ali, A.; Altman, M. D.; Reddy, G. S.; Chellappan, S.; Kairys, V.; Ozen, A.; Cao, H.; Gilson, M. K.; Tidor, B.; Rana, T. M.; Schiffer, C. A. Evaluating the Substrate-Envelope Hypothesis: Structural Analysis of Novel HIV-1 Protease Inhibitors Designed to Be Robust against Drug Resistance. J. Virol. 2010, 84, 5368-5378.
(7) Varghese, V.; Mitsuya, Y.; Fessel, W. J.; Liu, T. F.; Melikian, G. L.; Katzenstein, D. A.; Schiffer, C. A.; Holmes, S. P.; Shafer, R. W. Prototypical Recombinant Multi-Protease-Inhibitor-Resistant Infectious Molecular Clones of Human Immunodeficiency Virus Type 1. Antimicrob. Agents Chemother. 2013, 57, 4290-4299.
(8) King, N. M.; Prabu-Jeyabalan, M.; Nalivaika, E. A.; Schiffer, C. A. Combating Susceptibility to Drug Resistance. Chem. Biol. 2004, 11, 1333-1338.
(9) de Meyer, S.; Vangeneugden, T.; van Baelen, B.; de Paepe, E.; van Marck, H.; Picchio, G.; Lefebvre, E.; de Bethune, M. P. Resistance Profile of Darunavir: Combined 24-Week Results from the Power Trials. AIDS Res. Hum. Retroviruses 2008, 24, 379-388.
(10) Prezista [Package Insert]; Janssen Therapeutics: Titusville, N.J.
(11) Swanstrom, R.; Erona, J. Human Immunodeficiency Virus Type-1 Protease Inhibitors: Therapeutic Successes and Failures, Suppression and Resistance. Pharmacol. Ther. 2000, 86, 145-170.
(12) Humphris-Narayanan, E.; Akiva, E.; Varela, R.; Ó Conchúir, S.; Kortemme, T. Prediction of Mutational Tolerance in HIV-1 Protease and Reverse Transcriptase Using Flexible Backbone Protein Design. PLoS Comput. Biol. 2012, 8, e1002639.
(13) Muzammil, S.; Ross, P.; Freire, E. A Major Role for a Set of Non-Active Site Mutations in the Development of HIV-1 Protease Drug Resistance. Biochemistry 2003, 42, 631-638.
(14) Agniswamy, J.; Shen, C. H.; Aniana, A.; Sayer, J. M.; Louis, J. M.; Weber, I. T. HIV-1 Protease with 20 Mutations Exhibits Extreme Resistance to Clinical Inhibitors through Coordinated Structural Rearrangements. Biochemistry 2012, 51, 2819-2828.
(15) Kozisek, M.; Lepsik, M.; Grantz Saskova, K.; Brynda, J.; Konvalinka, J.; Rezacova, P. Thermodynamic and Structural Analysis of HIV Protease Resistance to Darunavir-Analysis of Heavily Mutated Patient-Derived HIV-1 Proteases. FEBS J. 2014, 281, 1834-1847.
(16) Mahalingam, B.; Boross, P.; Wang, Y. F.; Louis, J. M.; Fischer, C. C.; Tozser, J.; Harrison, R. W.; Weber, I. T. Combining Mutations in HIV-1 Protease to Understand Mechanisms of Resistance. Proteins: Struct., Funct., Genet. 2002, 48, 107-116.
(17) Ragland, D. A.; Nalivaika, E. A.; Nalam, M. N.; Prachanronarong, K. L.; Cao, H.; Bandaranayake, R. M.; Cai, Y.; Kurt-Yilmaz, N.; Schiffer, C. A. Drug Resistance Conferred by Mutations Outside the Active Site through Alterations in the Dynamic and Structural Ensemble of HIV-1 Protease. J. Am. Chem. Soc. 2014, 136, 11956-11963.
(18) Shafer, R. W. Rationale and Uses of a Public HIV Drug-Resistance Database. J. Infect. Dis. 2006, 194, S51-S58.
(19) Rhee, S.-Y.; Gonzales, M. J.; Kantor, R.; Betts, B. J.; Ravela, J.; Shafer, R. W. Human Immunodeficiency Virus Reverse Transcriptase and Protease Sequence Database. Nucleic Acids Res. 2003, 31, 298-303.
(20) Tamura, K.; Stecher, G.; Peterson, D.; Filipski, A.; Kumar, S. Mega6: Molecular Evolutionary Genetics Analysis Version 6.0. Mol. Biol. Evol. 2013, 30, 2725-2729.
(21) Surleraux, D. L.; Tahri, A.; Verschueren, W. G.; Pille, G. M.; de Kock, H. A.; Jonckers, T. H.; Peeters, A.; De Meyer, S.; Azijn, H.; Pauwels, R.; de Bethune, M. P.; King, N. M.; Prabu-Jeyabalan, M.; Schiffer, C. A.; Wigerinck, P. B. Discovery and Selection of TMC114, a Next Generation HIV-1 Protease Inhibitor. J. Med. Chem. 2005, 48, 1813-1822.
(22) Hogg, R. V., Tanis, E. A., Zimmerman, D. L. Probability and Statistical Inference, 9th Edition; Pearson Higher Education: Upper Saddle River, N.J., 2015.
(23) De Meyer, S.; Azijn, H.; Surleraux, D.; Jochmans, D.; Tahri, A.; Pauwels, R.; Wigerinck, P.; de Bethune, M. P. Tmc114, a Novel Human Immunodeficiency Virus Type 1 Protease Inhibitor Active against Protease Inhibitor-Resistant Viruses, Including a Broad Range of Clinical Isolates. Antimicrob. Agents Chemother. 2005, 49, 2314-2321.
(24) Sinha, N.; Smith-Gill, S. J. Protein Structure to Function Via Dynamics. Protein Pept. Lett. 2002, 9, 367-377.
(25) Condra, J. H.; Schleif, W. A.; Blahy, O. M.; Gabryelski, L. J.; Graham, D. J.; Quintero, J. C.; Rhodes, A.; Robbins, H. L.; Roth, E.; Shivaprakash, M.; et al. Vivo Emergence of HIV-1 Variants Resistant to Multiple Protease Inhibitors. Nature 1995, 374, 569-571.
(26) Nijhuis, M.; Schuurman, R.; de Jong, D.; Erickson, J.; Gustchina, E.; Albert, J.; Schipper, P.; Gulnik, S.; Boucher, C. A. Increased Fitness of Drug Resistant HIV-1 Protease as a Result of Acquisition of Compensatory Mutations During Suboptimal Therapy. AIDS 1999, 13, 2349-2359.
(27) Erickson, J. W. The Not-So-Great Escape. Nat. Struct. Biol. 1995, 2, 523-529.
(28) Hoffman, N. G.; Schiffer, C. A.; Swanstrom, R. Covariation of Amino Acid Positions in HIV-1 Protease. Virology 2003, 314, 536-548.

(29) Skalova, T.; Dohnalek, J.; Duskova, J.; Petrokova, H.; Hradilek, M.; Soucek, M.; Konvalinka, J.; Hasek, J. HIV-1 Protease Mutations and Inhibitor Modifications Monitored on a Series of Complexes. Structural Basis for the Effect of the A71v Mutation on the Active Site. *J. Med. Chem.* 2006, 49, 5777-5784.

(30) Meher, B. R.; Wang, Y. Interaction of I50/V Mutant and I50I/A71V Double Mutant HIV-Protease with Inhibitor Tmc114 (Darunavir): Molecular Dynamics Simulation and Binding Free Energy Studies. *J. Phys. Chem. B* 2012, 116, 1884-1900.

(31) Mittal, S.; Bandaranayake, R. M.; King, N. M.; Prabu-Jeyabalan, M.; Nalam, M. N.; Nalivaika, E. A.; Yilmaz, N. K.; Schiffer, C. A. Structural and Thermodynamic Basis of Amprenavir/Darunavir and Atazanavir Resistance in HIV-1 Protease with Mutations at Residue 50. *J. Virol.* 2013, 87, 4176-4184.

(32) Logsdon, B. C.; Vickrey, J. F.; Martin, P.; Proteasa, G.; Koepke, J. I.; Terlecky, S. R.; Wawrzak, Z.; Winters, M. A.; Merigan, T. C.; Kovari, L. C. Crystal Structures of a Multidrug-Resistant Human Immunodeficiency Virus Type 1 Protease Reveal an Expanded Active-Site Cavity. *J. Virol.* 2004, 78, 3123-3132.

(33) Chang, M. W.; Torbett, B. E. Accessory Mutations Maintain Stability in Drug-Resistant HIV-1 Protease. *J. Mol. Biol.* 2011, 410, 756-760.

(34) Appadurai, R.; Senapati, S. Dynamical Network of HIV-1 Protease Mutants Reveals the Mechanism of Drug Resistance and Unhindered Activity. *Biochemistry* 2016, 55, 1529-1540.

(35) Gulnik, S. V.; Suvorov, L. I.; Liu, B.; Yu, B.; Anderson, B.; Mitsuya, H.; Erickson, J. W. Kinetic Characterization and Cross-Resistance Patterns of HIV-1 Protease Mutants Selected under Drug Pressure. *Biochemistry* 1995, 34, 9282-9287.

(36) Collins, J. R.; Burt, S. K.; Erickson, J. W. Flap Opening in HIV-1 Protease Simulated by 'Activated' Molecular Dynamics. *Nat. Struct. Mol. Biol.* 1995, 2, 334-338.

(37) Weber, I. T.; Harrison, R. W. Molecular Mechanics Analysis of Drug-Resistant Mutants of HIV Protease. *Protein Eng., Des. Sel.* 1999, 12, 469-474.

(38) Jabara, C. B.; Jones, C. D.; Roach, J.; Anderson, J. A.; Swanstrom, R. Accurate Sampling and Deep Sequencing of the HIV-1 Protease Gene Using a Primer ID. *Proc. Natl. Acad. Sci. U.S.A.* 2011, 108, 20166-20171.

(39) Jacobson, M. P.; Friesner, R. A.; Xiang, Z.; Honig, B. On the Role of the Crystal Environment in Determining Protein Side-Chain Conformations. *J. Mol. Biol.* 2002, 320, 597-608.

(40) Jacobson, M. P.; Pincus, D. L.; Rapp, C. S.; Day, T. J.; Honig, B.; Shaw, D. E.; Friesner, R. A. A Hierarchical Approach to All-Atom Protein Loop Prediction. Proteins: Struct., *Funct., Genet.* 2004, 55, 351-367.

(41) Altschul, S. F.; Gish, W.; Miller, W.; Myers, E. W.; Lipman, D. J. Basic Local Alignment Search Tool. *J. Mol. Biol.* 1990, 215, 403-410.

(42) Shivakumar, D.; Williams, J.; Wu, Y.; Damm, W.; Shelley, J.; Sherman, W. Prediction of Absolute Solvation Free Energies Using Molecular Dynamics Free Energy Perturbation and the Opls Force Field. *J. Chem. Theory Comput.* 2010, 6, 1509-1519.

(43) Bowers, K. J.; Chow, E.; Xu, H.; Dror, R. O.; Eastwood, M. P.; Gregersen, B. A.; Klepeis, J. L.; Kolossvary, I.; Moraes, M. A.; Sacerdoti, F. D.; Salmon, J. K.; Shan, Y.; Shaw, D. E. Scalable Algorithms for Molecular Dynamics Simulations on Commodity Clusters. *Proceedings of the 2006 ACM/IEEE Conference on Supercomputing* 2006, 84.

(44) 2015-4, S. R., Desmond Molecular Dynamics System. D.E. *Shaw Research, Maestro-Desmond Interoperability Tools* 2015.

(45) Guo, Z.; Mohanty, U.; Noehre, J.; Sawyer, T. K.; Sherman, W.; Krilov, G. Probing the Alpha-Helical Structural Stability of Stapled P53 Peptides: Molecular Dynamics Simulations and *Analysis. Chem. Biol. Drug Des.* 2010, 75, 348-359.

(46) Jorgensen, W. L.; Chandrasekhar, J.; Madura, J. D.; Impey, R. W.; Klein, M. L. Comparison of Simple Potential Functions for Simulating Liquid Water. *J. Chem. Phys.* 1983, 79, 926-935.

(47) Ozen, A.; Sherman, W.; Schiffer, C. A. Improving the Resistance Profile of Hepatitis C Ns3/4a Inhibitors: Dynamic Substrate Envelope Guided Design. *J. Chem. Theory Comput.* 2013, 9, 5693-5705.

(48) Berendsen, H. J. C.; Postma, J. P. M.; van Gunsteren, W. F.; DiNola, A.; Haak, J. R. Molecular Dynamics with Coupling to an External Bath. *J. Chem. Phys.* 1984, 81, 3684-3690.

(49) Martyna, G. J.; Tobias, D. J.; Klein, M. L. Constant Pressure Molecular Dynamics Algorithms. *J. Chem. Phys.* 1994, 101, 4177-4189.

(50) Essmann, U.; Perera, L.; Berkowitz, M. L.; Darden, T.; Lee, H.; Pedersen, L. G. A Smooth Particle Mesh Ewald Method. *J. Chem. Phys.* 1995, 103, 8577-8593.

(51) Humphrey, W.; Dalke, A.; Schulten, K. VMD: Visual Molecular Dynamics. J. Mol. Graphics 1996, 14, 33-38.

(52) Ozen, A.; Haliloglu, T.; Schiffer, C. A. Dynamics of Preferential Substrate Recognition in HIV-1 Protease: Redefining the Substrate Envelope. *J. Mol. Biol.* 2011, 410, 726-744.

(53) Anderson, E.; Bai, Z.; Bischof, C.; Blackford, S.; Demmel, J.; Dongarra, J.; Du Croz, J.; Greenbaum, A.; Hammarling, S.; McKenney, A.; Sorensen, D. *LAPACK Users' Guide*, 3rd Edition; Society for Industrial and Applied Mathematics (SIAM): Philadelphia, Pa., 1999.

(54) Ragland, D.A., Elucidating the Interdependence of Drug Resistance From Combinations of Mutations, *J. Chem. Theory Comput.* 2017, 13, 5671-5682 (2017).

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A method of physically producing a ligand having increased potency against a protein target compared to a reference ligand, wherein the ligand possesses one or more of an increased binding affinity, an increased binding specificity, or an increased ability to avoid drug resistance, compared to the reference ligand, the method comprising the steps of:
   a) calculating a set of molecular dynamic trajectories of a protein-ligand complex family by conducting a series of molecular dynamic simulations that incorporate a binding affinity of the protein-ligand complex and at least one physical feature of the protein-ligand complex, wherein the protein-ligand complex family includes a plurality of ligands that includes the reference ligand and variants thereof, each of the plurality of ligands being bound to the protein target or one or more variants thereof, such that the protein-ligand complex family includes a plurality of protein-ligand complex pairs, the molecular dynamic trajectories of the protein-ligand complex simulating the mean occupancies of the bonds of the protein-ligand complex pairs;
   b) forming a set of tensors based on the molecular dynamic trajectories, the forming of the set of tensors including forming a respective tensor for each protein-ligand complex pair of the protein-ligand complex family, wherein each tensor is a set of physical properties for a member of the protein-ligand complex family;
   c) integrating the set of tensors with experimental binding data corresponding to each member of the protein-ligand complex family and assessing binding of each ligand to the protein target or variant thereof in each protein-ligand complex pair based on the simulated mean occupancies of the bonds of the protein-ligand complex pairs, wherein assessing the binding further includes one or more of:
   comparatively analyzing structure among the protein-ligand complex pairs;
   (ii) identifying effective changes in amino acid sequence of the protein target that promote drug resistance; and
   (iii) determining the binding affinity between the protein target and ligand of each protein-ligand pair;
   d) determining subsites in the ligand that can be changed to improve binding affinity, binding specificity or ability to avoid drug resistance, or a combination thereof, based on a difference of an original occupancy and the simulated mean occupancies; and
   e) incorporating into a ligand one or more changes at the subsites determined in (d), to physically produce an improved ligand having an increased binding affinity, binding specificity or ability to avoid drug resistance.

2. The method of claim 1, wherein the protein target includes an active binding site, and at least one site that is distinct from the active binding site and affects affinity of the ligand.

3. The method of claim 2, wherein the protein target is selected from the group consisting of HIV-1 protease, Hepatitis C NS3/4A protease, Influenza Neuraminidase, and human kinases.

4. The method of claim 1, wherein the ligand is a small molecule or therapeutic biologic.

5. The method of claim 1, wherein the at least one physical feature of the protein-ligand complex includes at least one member of the group consisting of: hydrogen bonding; van der Waals interaction; water structure; correlated motion; internal distances; and at least one of root mean square deviation and root mean square fluctuation of atoms of the protein or ligand or both the protein and ligand of the protein-ligand complex.

6. The method of claim 5, wherein hydrogen bonding is of the protein of the protein-ligand complex.

7. The method of claim 5, wherein hydrogen bonding is of the ligand of the protein-ligand complex.

8. The method of claim 5, wherein hydrogen bonding is of both the protein and the ligand of the protein-ligand complex.

9. The method of claim 5, wherein the van der Waals interaction is of the protein of the protein-ligand complex.

10. The method of claim 5, wherein the van der Waals interaction is of the ligand of the protein-ligand complex.

11. The method of claim 5, wherein the van der Waals interaction is of both the protein and the ligand of the protein-ligand complex.

12. The method of claim 5, wherein the water structure is of the protein of the protein-ligand complex.

13. The method of claim 5, wherein the water structure is of the ligand of the protein-ligand complex.

14. The method of claim 5, wherein the water structure is the protein and the ligand of the protein-ligand complex.

15. The method of claim 5, wherein the correlated motion includes at least one member of the group consisting of mutual information and a correlation coefficient matrix.

16. The method of claim 5, wherein the internal distance includes a distance difference plot.

17. The method of claim 5, wherein at least one of the root mean square derivation and root mean square fluctuation is the protein of the protein-ligand complex.

18. The method of claim 5, wherein at least one of the root mean square deviation and the root mean square fluctuation is of the ligand of the protein-ligand complex.

19. The method of claim 5, wherein at least one of the root mean square deviation and the root mean square fluctuation is the protein and the ligand of the protein-ligand complex.

20. The method of claim 1, wherein the protein-ligand complex family includes a plurality of variants of a protein, each of which is bound to the protein, wherein the protein-ligand complex family includes a plurality of protein-ligand pairs.

21. The method of claim 1, wherein forming the set of tensors includes forming a tensor for each protein-ligand complex pair of the protein-ligand complex family.

22. The method of claim 1, wherein analyzing the structure includes analyzing at least one of the group consisting of: hydrogen bonding; van der Waals force; water structure; correlated motion; internal distances; and at least one of root mean square deviation and root mean square fluctuation of atoms of the protein, or ligand, or both the protein and ligand of the protein-ligand complex.

23. The method of claim 1, further comprising analyzing the ligands for a better fit to a substrate envelope in the protein target, an ability to avoid the influence of remote changes in the protein target that contribute to drug resistance, or a combination thereof.

24. The method of claim 1, wherein the ligand is a protease inhibitor.

25. The method of claim 1, further comprising:
administering the one or more improved ligands to a subject in need thereof to treat a disease or condition.

* * * * *